(12) United States Patent
Aranyi et al.

(10) Patent No.: US 7,348,327 B2
(45) Date of Patent: Mar. 25, 2008

(54) COMPOUNDS

(75) Inventors: Peter Aranyi, Budapest (HU); Laszlo Balazs, God, Toth Arpad (HU); Imre Bata, Budapest (HU); Sandor Batori, Budapest (HU); Eva Boronkay, Budapest (HU); Philippe Bovy, Mareil Marly (FR); Karoly Kanai, Budapest (HU); Zoltan Kapui, Budapest (HU); Edit Susan, Dunakeszi, Hargita (HU); Tibor Szabo, Budapest (HU); Lajos T. Nagy, Budapest (HU); Katalin Urban-Szabo, Budapest (HU); Marton Varga, Dunakeszi (HU)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 10/507,005

(22) PCT Filed: Mar. 4, 2003

(86) PCT No.: PCT/HU03/00017

§ 371 (c)(1),
(2), (4) Date: Jan. 31, 2005

(87) PCT Pub. No.: WO03/074500

PCT Pub. Date: Sep. 12, 2003

(65) Prior Publication Data

US 2005/0130981 A1  Jun. 16, 2005

(30) Foreign Application Priority Data

Mar. 6, 2002  (HU) .................... 0200849

(51) Int. Cl.
| C07D 401/04 | (2006.01) |
| C07D 403/04 | (2006.01) |
| C07D 211/06 | (2006.01) |
| A61K 31/444 | (2006.01) |
| A61K 31/4545 | (2006.01) |
| A61K 31/497 | (2006.01) |
| A61K 31/501 | (2006.01) |

(52) U.S. Cl. .................. 514/252.03; 514/255.05; 514/318; 544/238; 544/364; 564/193

(58) Field of Classification Search ............... 514/321, 514/326, 255.05, 252.03, 318; 546/198, 546/208, 193; 544/238, 364
See application file for complete search history.

(56) References Cited

U.S. PATENT DOCUMENTS

| 3,225,037 A | 12/1965 | Zenitz et al. |
| 4,001,422 A | 1/1977 | Danilewicz et al. |
| 2004/0242636 A1* | 12/2004 | Haffner et al. .............. 514/326 |
| 2005/0176771 A1* | 8/2005 | Hayakawa et al. .......... 514/326 |

FOREIGN PATENT DOCUMENTS

| EP | 0 156 433 A | 10/1985 |
| EP | 1308439 | 5/2003 |
| JP | 20020264450 | * 9/2002 |
| WO | WO 98 19998 A | 5/1998 |
| WO | WO 99 65895 A | 12/1999 |
| WO | WO 01 96295 A | 12/2001 |
| WO | WO 02 30890 A | 4/2002 |
| WO | WO 02 38541 A | 5/2002 |
| WO | WO 02 51836 A | 7/2002 |
| WO | WO 03 000250 A | 1/2003 |
| WO | WO 03 002531 A | 1/2003 |
| WO | WO 03 002553 A | 1/2003 |

OTHER PUBLICATIONS

Database Crossfire Beilstein 'Online!'; Beilstein Institut zur Forderung der Chemishen Wissenschaften, Frankfurt am Main, DE; Beilstein Registry No. 402384 & J. Med. Chem., vol. 17, 1974, pp. 739, 742; XP002242780.
Database Crossfire Beilstein 'Online!'; Beilstein Institut zur Forderung der Chemishen Wissenschaften, Frankfurt am Main, DE; Beilstein Registry No. 8616397 & J. Med. Chem., vol. 43, No. 11, 2000, pp. 2087-2092; XP002242788.
Carling, R.W., et al; "1-(3-Cyanobenzylpiperidin-4-yl)-5-methyl-4-phenyl-1,3-dyhdroimidazol-2-one: A Selective High-Affinity Antagonist for the Human Dopamine D4 Receptor with Excellent Selectivity over Ion Channels"; J. Med. Chem. 1999, 42, pp. 2706-2715.
Moon, Sung-Hawn, et al; "An Efficient Conversion of Chiral α-Amino Acids to Enantiomerically Pure 3-Amino Cyclic Amines"; Synthetic Communications; 1998; 28(21); pp. 3919-3926.
Demange, Luc, et al; "Practical Synthesis of Boc and Fmoc Protected 4-Fluoro and 4-Difluoroprolines from Trans-4-Hydroxyproline"; Tetrahedron Letters, 39, 1998, pp. 1169-1172.
Augustyns, K.J.L.; "Pyrrolidides: synthesis and structure-activity relationship as inhibitors of dipeptidyl petidase IV"; European Journal of Medicinal Chemistry; vol. 32; No. 4; 1997; pp. 301-309; XP004086653.
Database Crossfire Beilstein 'Online!'; Beilstein Institut zur Forderung der Chemishen Wissenschaften, Frankfurt am Main, DE; Beilstein Registry No. 6688440 & J. Med. Chem., vol. 36, No. 23, 1993, pp. 3707-3720; XP002242778.
Database Crossfire Beilstein 'Online!'; Beilstein Institut zur Forderung der Chemishen Wissenschaften, Frankfurt am Main, DE; Beilstein Registry No. 4298035 & J. Med. Chem., vol. 34, No. 2, 1991, pp. 656-663; XP002242779.
Hughes, et al, NVP-DPP728 (1-[[[2-[(5-Cyanopyridin-2-yl)amino]ethyl]amino]acetyl]-2-cyano-(S)-pyrrolidine), a Slow-Binding Inhibitor of Dipeptidyl Peptidase IV; Biochemistry, vol. 38, 1999, pp. 11597-11603.

* cited by examiner

Primary Examiner—Rebecca Anderson
Assistant Examiner—Michael P. Barker
(74) Attorney, Agent, or Firm—Barbara E. Kurys

(57) ABSTRACT

The present invention relates to new, potent DPP-IV enzyme inhibitors of the general formula (I), which contain fluorine atoms.

22 Claims, 3 Drawing Sheets

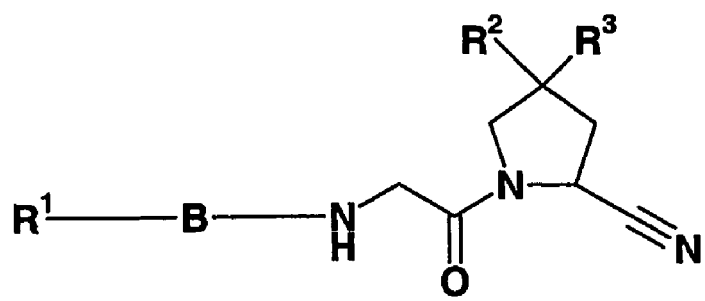
(I) Fig. 1
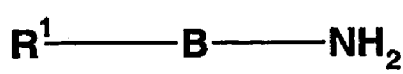
(II) Fig. 2
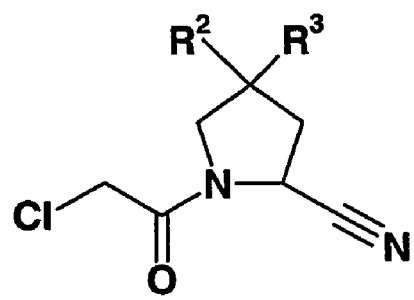
(III) Fig. 3
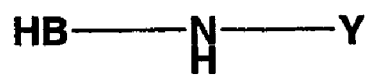
(IV) Fig. 4
(V) Fig. 5

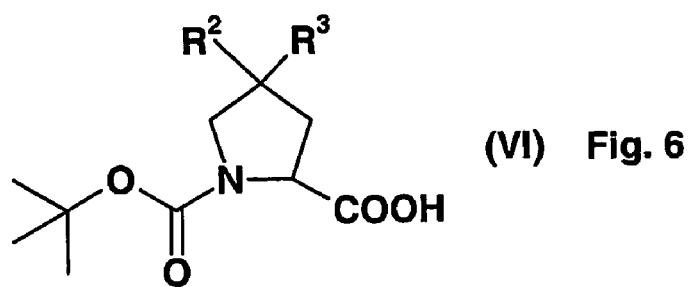
(VI) Fig. 6
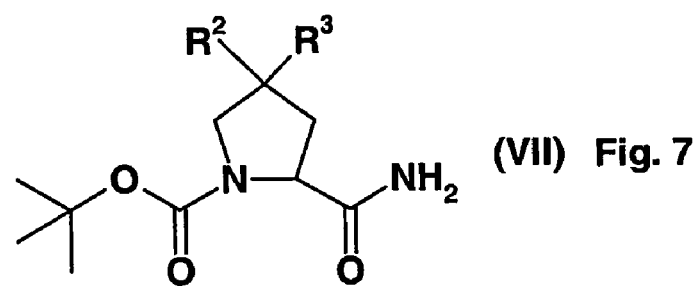
(VII) Fig. 7
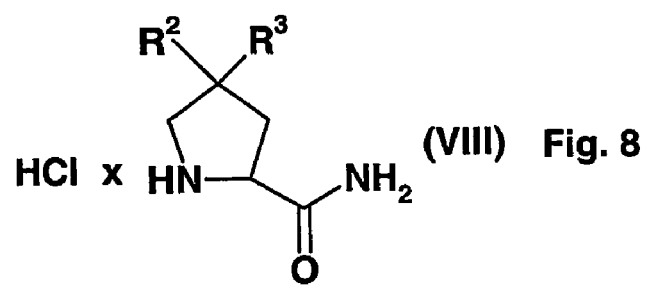
(VIII) Fig. 8
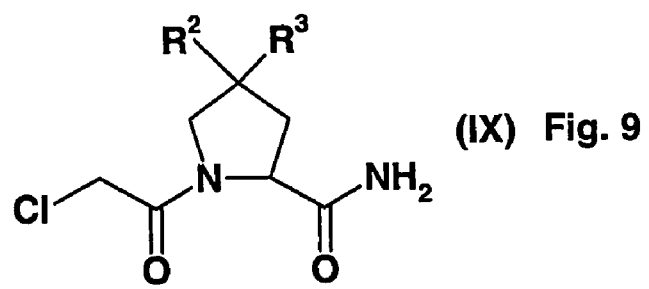
(IX) Fig. 9
(X) Fig. 10

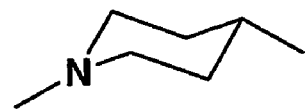 (1) Fig. 11
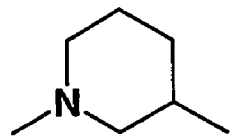 (2) Fig. 12
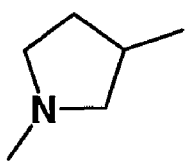 (3) Fig. 13
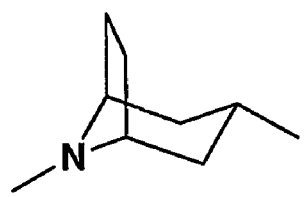 (4) Fig. 14
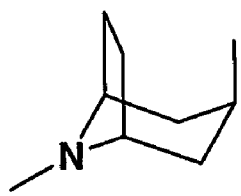 (5) Fig. 15
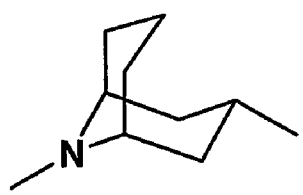 (6) Fig. 16
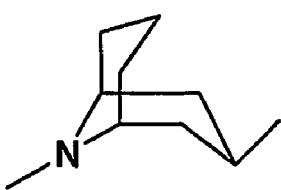 (7) Fig. 17

COMPOUNDS

The present invention relates to the novel compound of the general formula (I) possessing dipeptidyl-peptidase-IV enzyme inhibitory activity, as well as their salts, solvates and isomers, to the therapeutic application of the compounds of the general formula (I), to the pharmaceutical compositions containing the compounds of the general formula (I), to the process for their preparation and to the new intermediates of the general formulae (II), (III), (V), (VII), (VI) and (IX).

The enzyme dipeptidyl-peptidase-IV (DPP-IV), which is identical with the lymphocyte surface glycoprotein CD26, a polypeptide with the molar mass of 110 k Dalton, is formed in the tissues and organs of mammals. This enzyme can be found, among others, in the liver, in the Langerhans islets, in the renal cortex, in the lungs, and in certain tissues of the prostate and small intestine. Significant DPP-IV activity can be observed furthermore in the body fluids (as for instance in the plasma, serum and urine).

DPP-IV is a serine protease type enzyme, which has the unique specificity to cleave dipeptides from the N-terminals of peptides where the penultimate amino acid is primarily proline, alanine or hydroxy proline.

DPP-IV enzyme is responsible for the decomposition of the glucagon-like peptides, peptide-1 (GLP-1) and peptide-2 (GLP-2) in the body. The enzyme GLP-1 strongly stimulates the insulin production of the pancreas, thus it has a direct, favourable effect on the glucose homeostasis, therefore DPP-IV inhibitors are suitable for the treatment and prevention of non-insulin dependent diabetes mellitus (NIDDM) and other diseases related with the DPP-IV enzyme activity including but not limited to diabetes, obesity, hyperlipidemia, dermatological or mucous membrane disorders, poriasis, intestinal distress, constipation, autoimmune disorders such as enchephalomyelitis, complement mediated disorders such as glomerulonepritis, lipodystrophy, and tissue damage, psychosomatic, depressive, and neurophsychiatric disease such as anxiety, depression, insomnia, schizophrenia, epilepsy, spasm, and chronic pain, HIV infection, allergies, inflammation, arthritis, transplant rejection, high blood pressure, congestive heart failure, tumors, and stress-induced abortions.

Our aim was to prepare new, effective, stable and safe DPP-IV inhibitors.

We have found that the compounds of the general formula (I) wherein $R^1$ stands for:

a nitrogen-containing aromatic moiety consisting of one or two aromatic rings, preferably pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl, benzisoxazolyl, tetrazolyl or triazinyl rings; which are, optionally, mono- or disubstituted independently from each other by one or two of the following groups: C1-4 alkyl groups, C1-4 alkoxy groups, halogen atom, trihalogenomethyl group, methylthio group, nitro group, cyano group, amino group or phenyl group; or thienyl or furyl or benzyl group; or p-toluenesulfonyl group; or the acyl group of formula $R_{1a}$—CO, wherein $R_{1a}$ means C1-4 alkyl group, phenyl group; phenyl, pyridyl or phenylethenyl group substituted with one or more C1-4 alkyl- and/or C1-4 alkoxy- or nitro-group or halogen atom; phenylethenyl group, or a phenylethyl group substituted with alkylene-dioxy group; piperidin-1-yl, 4-methyl-piperazin-1-yl, or pyrrolidin-1-yl group;

B stands for a group according to the formula (1) or (2) or (3) or (4) or (5) or (6) or (7);

$R^2$ stands for hydrogen atom or fluoro atom;

$R^3$ stands for fluoro atom—as well as the salts, isomers and solvates of these compounds have significant advantages as regards their activity, duration of action, stability and toxicity in comparison with the state of the art.

In agreement with the accepted terminology, the configuration of carbon atom in position 2 of the fluoropyrrolidine group is favourably S, whereas that of carbon atom in position 4 is S or R.

One embodiment of the present invention includes compounds of the general formula (I)—wherein $R^1$ means a nitrogen-containing aromatic moiety consisting of one or two aromatic rings, preferably a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl ring; which is, in a given case, independently from each other mono- or disubstituted by one or two of the following groups: C1-4 alkyl groups, C1-4 alkoxy groups, halogen atom, trihalogenomethyl group, methylthio group, nitro group, cyano group; or thienyl or furyl group; or p-toluenesulfonyl group; or acyl group of formula $R_{1a}$—CO, wherein $R_{1a}$ means C1-4 alkyl group, phenyl group; phenyl, pyridyl or phenylethenyl group substituted with one or more alkyl- and/or alkoxy- or nitro-group or halogen atom; phenylethenyl or phenylethyl group substituted with alkylene-dioxy group; piperidin-1-yl, 4-methylpiperazin-1-yl, pyrrolidin-1-yl group, B stands for a group of formula (1) or (2) or (3) or (4) or (5) or (6) or (7);

$R^2$ stands for hydrogen atom or fluorine atom;

$R^3$ stands for fluorine atom—and salts, isomers, tautomers solvates and hydrates thereof.

Another embodiment of the present invention includes compounds of the general formula (I)—wherein $R^1$ means a nitrogen-containing aromatic moiety consisting of one or two aromatic rings, preferably a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl ring; which is, in a given case, independently from each other mono- or disubstituted by one or two of the following groups: C1-4 alkyl groups, C1-4 alkoxy groups, halogen atom, trihalogenomethyl group, methylthio group, nitro group, cyano group; or a thienyl or furyl group; or a p-toluenesulfonyl group; or an acyl group of formula $R_{1a}$—CO, wherein $R_{1a}$ means C1-4 alkyl group, phenyl group; phenyl, pyridyl or phenylethenyl group substituted with one or more alkyl- and/or alkoxy- or nitro-group or halogen atom; phenylethenyl or phenylethyl group substituted with alkylene-dioxy group; piperidin-1-yl, 4-methylpiperazin-1-yl, pyrrolidin-1-yl group, B stands for a group of formula (1);

$R^2$ stands for hydrogen atom or fluorine atom;

$R^3$ stands for fluorine atom—and salts, isomers, tautomers solvates and hydrates thereof.

Another embodiment of the present invention includes compounds of the general formula (I)—wherein $R^1$ means a nitrogen-containing aromatic moiety consisting of one or two aromatic rings, preferably a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl ring; which is, in a given case, independently from each other mono- or disubstituted by one or two of the following groups: C1-4 alkyl groups, C1-4 alkoxy groups, halogen atom, trihalogenomethyl group, methylthio group, nitro group, cyano group; or a thienyl or furyl group; or a p-toluenesulfonyl group; or an acyl group of formula $R_{1a}$—CO, wherein $R_{1a}$ means C1-4 alkyl group, phenyl group; phenyl, pyridyl or phenylethenyl group substituted with one or more alkyl- and/or alkoxy- or nitro-group or halogen atom; phenylethenyl or phenylethyl group substituted with alkylene-dioxy group; piperidin-1-yl, 4-methylpiperazin-1-yl, pyrrolidin-1-yl group, B stands for a group of formula (2);

$R^2$ stands for hydrogen atom or fluorine atom;

$R^3$ stands for fluorine atom—and salts, isomers, tautomers solvates and hydrates thereof.

Another embodiment of the present invention includes compounds of the general formula (I)—wherein $R^1$ means a nitrogen-containing aromatic moiety consisting of one or two aromatic rings, preferably a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl ring; which is, in a given case, independently from each other mono- or disubstituted by one or two of the following groups: C1-4 alkyl groups, C1-4 alkoxy groups, halogen atom, trihalogenomethyl group, methylthio group, nitro group, cyano group; or a thienyl or furyl group; or a p-toluenesulfonyl group; or an acyl group of formula $R_{1a}$—CO, wherein $R_{1a}$ means C1-4 alkyl group, phenyl group; phenyl, pyridyl or phenylethenyl group substituted with one or more alkyl- and/or alkoxy- or nitro-group or halogen atom; phenylethenyl or phenylethyl group substituted with alkylene-dioxy group; piperidin-1-yl, 4-methylpiperazin-1-yl, pyrrolidin-1-yl group, B stands for a group of formula (3);

$R^2$ stands for hydrogen atom or fluorine atom;

$R^3$ stands for fluorine atom— and salts, isomers, tautomers solvates and hydrates thereof.

Another embodiment of the present invention includes compounds of the general formula (I)—wherein $R^1$ means a nitrogen-containing aromatic moiety consisting of one or two aromatic rings, preferably a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl ring; which is, in a given case, independently mono- or disubstituted by one or two of the following groups: C1-4 alkyl groups, C1-4 alkoxy groups, halogen atom, trihalogenomethyl group, methylthio group, nitro group, cyano group; or a thienyl or furyl group; or a p-toluenesulfonyl group; or an acyl group of formula $R_{1a}$—CO, wherein $R_{1a}$ means C1-4 alkyl group, phenyl group; phenyl, pyridyl or phenylethenyl group substituted with one or more alkyl- and/or alkoxy- or nitro-group or halogen atom; phenylethenyl or phenylethyl group substituted with alkylene-dioxy group; piperidin-1-yl, 4-methylpiperazin-1-yl, pyrrolidin-1-yl group, B stands for a group of formula (4) or (5);

$R^2$ stands for hydrogen atom or fluorine atom;

$R^3$ stands for fluorine atom—and salts, isomers, tautomers solvates and hydrates thereof.

Another embodiment of the present invention includes compounds of the general formula (I)—wherein $R^1$ means a nitrogen-containing aromatic moiety consisting of one or two aromatic rings, preferably a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl, benzoxazolyl or benzisoxazolyl ring; which is, in a given case, independently mono- or disubstituted by one or two of the following groups: C1-4 alkyl groups, C1-4 alkoxy groups, halogen atom, trihalogenomethyl group, methylthio group, nitro group, cyano group; or a thienyl or furyl group; or a p-toluenesulfonyl group; or an acyl group of formula $R_{1a}$—CO, wherein $R_{1a}$ means C1-4 alkyl group, phenyl group; phenyl, pyridyl or phenylethenyl group substituted with one or more alkyl- and/or alkoxy- or nitro-group or halogen atom; phenylethenyl or phenylethyl group substituted with alkylene-dioxy group; piperidin-1-yl, 4-methylpiperazin-1-yl, pyrrolidin-1-yl group, B stands for a group of formula (6) or (7);

$R^2$ stands for hydrogen atom or fluorine atom;

$R^3$ stands for fluorine atom—and salts, isomers, tautomers, solvates and hydrates thereof.

Preferred compound of the general formula (I) are wherein R1, B or R2 and R3 are those groups which are listed in Tables 1 to 3 including any combinations thereof, for example (2S)-4,4-difluoro-1-(2-{[8-(2-pyrimidinyl)-8-azabicyclo[3.2.1]oct-3-yl]exo-amino}acetyl)-2-pyrrolidine carbonitrile; (2S,4S)-4-fluoro-1-(2-{[8-(2-pyrazinyl)-8-azabicyclo-[3.2.1]-oct-3-yl]exo-amino}acetyl)-2-pyrrolidinecarbonitrile; (2S)-4,4-Difluoro-1-(2-{[1-(2-pyrazinyl)piperidin-4-yl]amino}acetyl)-2-pyrrolidine carbonitrile; (2S)-4,4-Difluoro-1-(2-{[1-(5-cyanopyridin-2-yl)piperidin-4-yl]amino}acetyl)-2-pyrrolidine carbonitrile; (2S)-4,4-Difluoro-1-(2-{[1-(6-chloropyridazin-3-yl)piperidin-4-yl]

amino}acetyl)-2-pyrrolidine carbonitrile; (2S)-4,4-Difluoro-1-(2-{[1-(6-cyanopyridazin-3-yl)piperidin-4-yl]amino}acetyl)-2-pyrrolidine carbonitrile;

Term "nitrogen containing aromatic moiety consisting of one or two aromatic rings" includes all such ring systems known at the priority date of our present patent application.

Term "halogen atom" means fluorine, chlorine, bromine, or iodine atom. "C1-4 alkyl group" and "C1-4 alkoxy group" mean linear or branched chain aliphatic hydrocarbon groups containing 1-4 carbon atoms.

The compounds of the general formula (I) according to our invention can be prepared by the alkylation of the primary amines of the general formula (II)—wherein the meanings of $R^1$ and B are the same as given above—with the chloroacetyl derivative of the general formula (III)—wherein the meanings of $R^2$ and $R^3$ are as given above—and, if desired, by transforming the resulting compounds into one of their salts or solvates (Scheme 1).

In the course of the alkylation the chloroacetyl derivatives of the general formula (III) are applied in excess, and the resulting hydrogen chloride is bound by various acid binding agents, preferably by a base, such as for instance triethylamine, potassium carbonate, 1,8-diazabicyclo[5.4.0]undec-7-ene (DBU) or 2-terc-butylimino-2-diethylamino-1,3-dimethyl-perhydro-1,3,2-diazaphosphorine—bound to a resin (PBEMP)—, which is known as super base. The reaction is preferably performed at a temperature between 25 and 70° C.

The primary amines of the general formula (II) are prepared in a two-step synthesis (Scheme 2). In the first step the starting cyclic secondary amine of the general formula (IV)—wherein the meaning of Y is hydrogen atom, acetyl, or tert-butoxycarbonyl group—are arylated, preferably with the aryl halogenides of the general formula (X), wherein the meaning of $R^1$ is the same as given above and X stands for halogen atom. Depending on the meaning of $R^1$ the arylation reaction can be carried out in polar, protic or aprotic solvents, between 25 and 150° C., preferably in alcohols (ethanol, n-butanol, n-pentanol), or without solvent in microwave oven, using an acid binder, for instance the excess of the amine, or DBU.

For starting material the free amines or protected secondary amines of the general formula (IV)—known from the literature—are used, thus 4-acetaminopiperidine (B=formula (1), Y=COCH$_3$) (U.S. Pat. No. 3,225,037); 4-tert-butoxycarbonylaminopiperidine (B=formula (1), Y=COOC(CH$_3$)$_3$) (J. Med. Chem. 1999, 42, 2706); 3-(S)-tert-butoxycarbonylaminopiperidine (B=formula (2)) and 3-(S)-tert-butoxycarbonylaminopyrrolidine (B=formula (3)) (Synth. Comm. 1998, 28, 3919) in the last two cases Y=COOC(CH$_3$)$_3$; tert-butyl 8-azabicyclo[3.2.1]-oct-3-yl-exo-carbamate (B=formula (4), tert-butyl 8-azabicyclo[3.2.1]-oct-3-yl-endo-carbamate (B=formula (5)) (J. Med. Chem 1991, 34, 656), tert-butyl-9-azabicyclo[3.3.1]-non-3-yl-exo-carbamate (B=formula (6)) and tert-butyl-9-azabicyclo-[3.3.1]-non-3-yl-endo-carbamate (B=formula (7)), (J. Med. Chem 1993, 36, 3720)) (Y=COOC(CH$_3$)$_3$).

In the second step the protecting group Y is removed from the arylated amine of the general formula (V)—wherein the meanings of $R^1$ and B are the same as defined above—by acidic hydrolysis. The reaction is carried out in aqueous hydrochloric acid or in ethanolic hydrogen chloride solution at a temperature between 25 and 78° C. to yield the aliphatic or cyclic primary amines of the general formula (II)—wherein the meanings of $R^1$ and B are the same as defined above.

If $R^1$ stands for an acyl group of formula $R_{1a}$—CO, the compounds of the general formula (IV)—wherein the meaning of Y is tert-butoxycarbonyl group—are reacted with the acid derivatives of the general formula $R^{1a}$—COZ—wherein the meaning of Z is a leaving group, preferably a chloro atom—advantageously at a temperature around 0° C., by using an inorganic or organic base, preferably triethylamine as acid binding agent. From the compounds of the general formula (V) the protecting group Y is cleaved under acidic conditions, preferably by use of trifluoroacetic acid in dichloromethane solution, at 0-30° C., to obtain the the amines of the general formula (II), wherein the meaning of $R^1$ is the group of formula $R_{1a}$—CO.

The 1-(2-chloroacetyl)-2-pyrrolidinecarbonitriles of the general formula (III)—wherein the meanings of $R^2$ and $R^3$ are the same as defined above—are prepared in a four-step synthesis (Scheme 3).

The starting compounds are the fluoroproline derivatives, preferably L-fluoroproline derivatives—wherein the meanings of $R^2$ and $R^3$ are the same as defined above—with a nitrogen protected with tert-butoxycarbonyl group. These compounds can be prepared by methods written in the literature (Tetrahedron Lett. 1998, 39, 1169). In the first step a mixed anhydride is prepared with pivaloyl chloride or chloroformic acid ethyl ester, then the carbamoyl derivatives of the general formula (VII)—wherein the meanings of $R^2$ and $R^3$ are the same as defined above—are formed.

The reaction is preferably carried out in a halogenated solvent (CHCl$_3$, CH$_2$Cl$_2$), at 0-25° C.

In the second step the tert-butoxycarbonyl group is cleaved in ethanolic hydrogen chloride solution. The hydrolysis takes place at 0-25° C. and the hydrochlorides of the carboxamides of the general formula (VIII)—wherein the meanings of $R^2$ and $R^3$ are the same as defined above—are obtained.

The fluoropyrrolidinecarboxamides of the general formula (VIII) thus obtained are in the third step acylated with chloroacetyl chloride, preferably at 0° C., in a halogenated solvent (CHCl$_3$, CH$_2$Cl$_2$). Thus the chloroacetylcarbamoyl derivatives of the general formula (IX)—wherein the meanings of $R^2$ and $R^3$ are the same as defined above are formed.

In the fourth step the chloroacetylcarbamoyl derivatives of the general formula (IX) are dehydrated to yield the chloroacetylcyano derivatives of the general formula (III)—wherein the meanings of $R^2$ and $R^3$ are the same as defined above. Dehydration is preferably carried out with phosphorous oxychloride in dichloromethane at the boiling point of the reaction mixture.

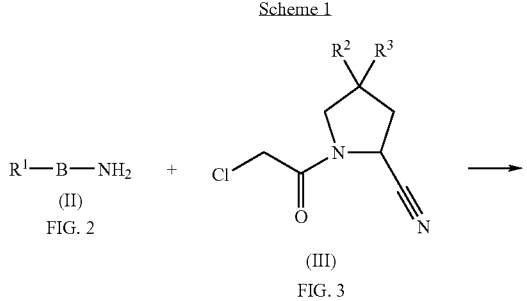

Scheme 1

(II)

(III)

FIG. 2

FIG. 3

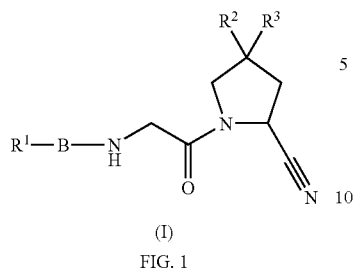

(I)
FIG. 1

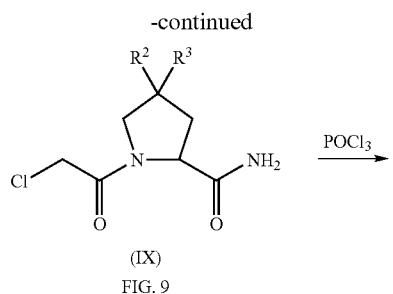

(IX)
FIG. 9

Scheme 2

HB—N—Y  →  R¹—B—N—Y  →
   H          (X)        H
              FIG. 10
(IV)         (V)
FIG. 4       FIG. 5

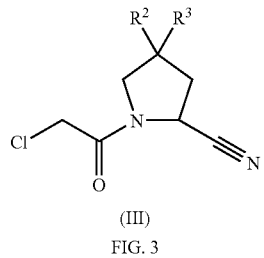

(III)
FIG. 3

R¹—B—NH₂

(II)
FIG. 2

Biological Investigations

DPP-IV enzyme inhibitory activities of the compounds with the general formula (I) were determined by the following method:

|  | Applied conditions of the assay: |
|---|---|
| DPP-IV. source: | solubilized crude extractum from CaCo/Tc-7 cells content: 0.8-1 µg/assay |
| Substrate: | H-Gly-Pro-AMC (Bachem) |
| Reaction: | 1 hour preincubation with samples at 37° C., 30 min reaction time at 37° C. |
| Stop solution: | 1M Na-acetate buffer (pH = 4.2) |
| Reaction mixture: | 10 µl enzyme solution |
|  | 10 µl test compound or assay buffer |
|  | 55 µl assay buffer |
|  | 25 µl substrate |
|  | 300 µl stop solution |
| Measurement: | spectrofluorometric determination by Tecan plate reader (Ex: 360 nm   Em: 465 nm) |

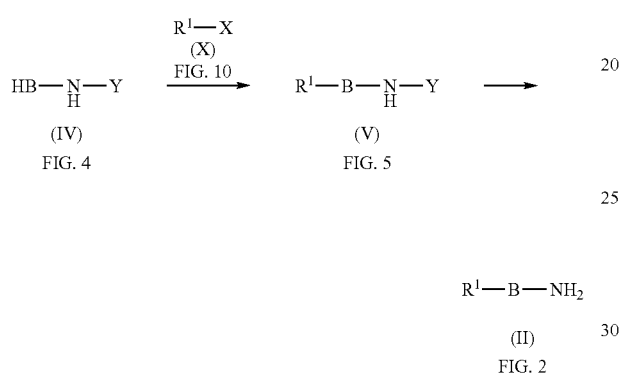

Scheme 3

(VI)
FIG. 6

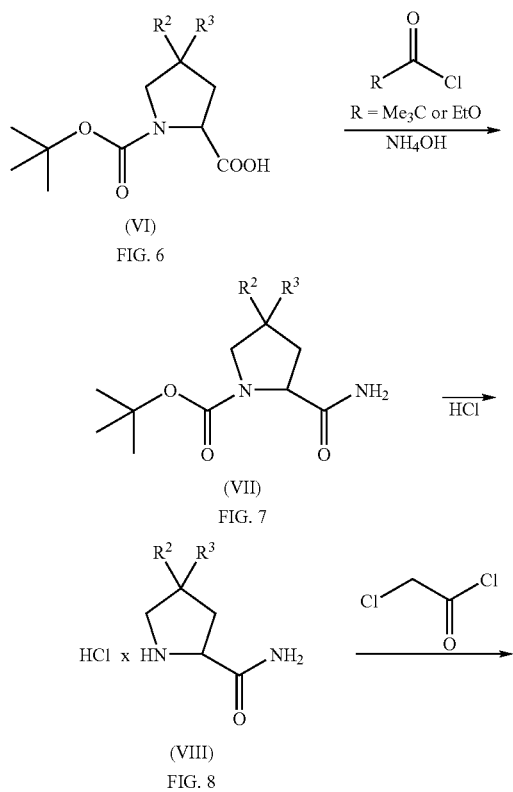

(VII)
FIG. 7

(VIII)
FIG. 8

The reaction of the DPP-IV enzyme and the H-Gly-Pro-AMC substrate is recorded by the liberation of AMC (7-amino-4-methylcoumarin) at 37° C. in 100 mM Tris-HCl, pH=7.5 (assay buffer). Standard curve of AMC is linear up to 31.25 µM concentration, that is why we used the relative fluorescence unit (RFU) of the AMC formed. It is detected by using 360 nm excitation and 465 emission filters (30 µs integration time, Gain 25, No. of Flashes 50) by Tecan Spectrofluor Plus plate reader. Under these conditions enzyme reaction is linear for at least 30 min, and the enzyme dependence is linear up to 2.5 µg protein (up to 700 RFU). Using 1-0.8 µg of extracted protein $K_m$ for H-Gly-Pro-AMC is 50 µM. Substrate concentrations higher than 500 µM caused fluorescency detection problems (inner filter effect) that can be solved by dilution of the samples.

The assay is designed to detect the active inhibitors as efficiently as possible, using a 60 min preincubation time at 37° C. The assay is conducted by adding 0.8-1 µg protein extract in 10 µl enzyme solution (using assay buffer: 100 mM Tris-HCl, pH=7.5) to the wells containing the test compounds in 10 µl volume and the 55 µl assay buffer (65 µl assay buffer in the case of controls). After the preincubation period, the reaction is started by the addition of 25 µl 1 mM H-Gly-Pro-AMC substrate solution (250 µM final concentration). The final test volume is 100 µl and the test solution contains 1% DMSO coming from the test compounds solution. Reaction time is 30 min at 37° C., and the reaction is stopped by adding 300 µl 1 M Na-acetate buffer, pH=4.2. The fluorescence (RFU) of AMC formed is detected using 360 nm excitation and 465 emission filters in Tecan spectrofluor Plus plate reader (30 µs integration time, Gain 25 No. of Flashes 50). Inhibition % are calculated using the RFU of control and RFU of blank.

$IC_{50}$ values characteristic for the enzyme inhibitory effect of the compounds of the general formula (I) according to the invention are smaller than 100 nM.

The compounds of the general formula (I) and their salts solvates and isomers can be formulated to orally or parenterally applicable pharmaceutical compositions by methods known per se, by mixing them with one or more pharmaceutically accepted excipients and can be administered as a unitary dosage form.

The appropriate unitary dosage form comprise the oral forms, such as tablets, hard or soft gelatin capsules, powders, granules and oral solutions or suspensions, the sublingual, buccal, intratracheal, intraocular, intranasal forms, by inhalation, the topical, transdermal, sub-cutaneous, intra-muscular or intra-venous forms, the rectal forms and the implants. For the topical application, the compounds of the invention may be used as creams, gels, ointments of lotions.

As as example, a unitary dosage form for a compound according to the invention, in the form of a tablet, can comprise the following ingredients:

| | |
|---|---|
| A compound of the general formula (I) | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

Daily dose of the compounds of the general formula (I) may depend on several factors, thus the nature and seriousness of the disease of the patient, the mode of application and on the compound itself.

Further details of the invention are demonstrated by the examples below, without limiting the claims to the examples.

FIG. 1 shows compounds of the general formula (I),
FIG. 2 shows compounds of the general formula (II),
FIG. 3 shows compounds of the general formula (II),
FIG. 4 shows compounds of the general formula (IV),
FIG. 5 shows compounds of the general formula (V),
FIG. 6 shows compounds of the general formula (VI),
FIG. 7 shows compounds of the general formula (VII),
FIG. 8 shows compounds of the general formula (VII),
FIG. 9 shows compounds of the general formula (IX),
FIG. 10 shows compounds of the general formula (X),
FIG. 11 shows formula (1),
FIG. 12 shows formula (2),
FIG. 13 shows formula (3),
FIG. 14 shows formula (4),
FIG. 15 shows formula (5),
FIG. 16 shows formula (6),
FIG. 17 shows formula (7).

EXAMPLES

Example 1

(2S)-4,4-difluoro-1-(2-{[8-(2-pyrimidinyl)-8-azabi-cyclo[3.2.1]oct-3-yl]exo-amino}acetyl)-2-pyrrolidine Carbonitrile The meaning of $R^1$ is 2-pyrimidinyl group, B means a group of formula (4), $R^2$ and $R^3$ mean fluorine atom in general formula (I).

a.) tert-butyl 8-(2-pyrimidinyl)-8-azabicyclo[3.2.1]oct-3-yl-exo-carbamate with (V) General Formula—Where $R^1$ is 2-pyrimidinyl, Y is COOC$(CH_3)_3$, B is (4) Group 14.7 g of tert-butyl 8-azabicyclo[3.2.1]oct-3-yl-exo-carbamate (65 mmol) (J. Med. Chem. 1991, 34, 656) and 8.93 g of 2-chioropyrimidine (78 mmol) and 12.7 ml of 1.8-diazabicyclo[5.4.0]undec-7-ene (DBU) (85 mmol) are dissolved in 230 ml of 1-pentanol and heated under reflux for 4 hours. The solvents are evapotared and the residue is dissolved in 250 ml of chloroform and washed with 2×300 ml of water, dried over $Na_2SO_4$, and purified by column chromatography using n-hexane-ethyl acetate-chloroform (1:1:1) as eluent to result in white crystals which are triturated with n-hexane. Yield: 13.25 g (67%). M.p.: 113-115° C. $^1$H-NMR (400 MHz, $CDCl_3$): δ 1.34 (s, 9H), 1.49 (t, 2H), 1.66-1.97 (m, 6H), 3.89 (br, 1H), 4.61 (d, 2H), 6.60 (t+br, 1+1H), 8.34 (d, 2H).

b.) 8-(2-pyrimidinyl)-8-azabicyclo[3.2.1]oct-3-yl-exo-amine with (II) General Formula—Where $R^1$ and B are Given in Step 1a.)

13 g of tert-butyl 8-(2-pyrimidinyl)-8-azabicyclo[3.2.1]oct-3-yl-exo-carbamate (43 mmol) are dissolved in a mixture of 120 ml of trifluoroacetic acid and 120 ml of dichloromethane. The solution is stirred for 30 minutes and evapotared. The residue is dissolved in 50 ml of dichloromethane and evaporated. This method is repetead three times and the last organic solution is extracted with 100 ml of saturated aq. sodium carbonate solution. The layers are separated and the aqueous phase is washed with 4×50 ml of dichloromethane. The combined organic layers are dried over $Na_2SO_4$ and evaporated to result in a white powder which is triturated with n-hexane. Yield: 6.7 g (77%). M.p.: 56-59° C. $^1$H-NMR (400 MHz, DMSO-$d_6$): δ 1.29 (t, 2H), 1.64-1.98 (m, 6H), 3.19 (m, 1H), 4.58 (dd, 2H), 6.57 (t, 1H), 8.33 (d,2H).

c.) tert-butyl) (2S)-2-(aminocarbonyl)-4,4-difluoro-1-pyrrolidinecarboxylate of the General Formula (VII) Wherein $R^2$ and $R^3$ Mean Fluorine Atom 5.7 g (22.7 mmol) of tert-butyl (2S)-2-(aminocarbonyl)-4,4-difluoro-2-pyrrolidinecarboxylic acid (Tetraheron Lett. 1998, 39, 1169) are dissolved in 57 ml of dichloromethane and to the solution 3.8 ml (27.2 mmol) of triethylamine are added. To the resulting mixture dropwise, at −15° C. 3 ml (25 mmol) of pivaloyl chloride are added and the mixture is stirred at that temperature for 1 hour, then 7 ml of 25% aqueous ammonia solution are added drop wise and the mixture is stirred for 1 hour. The reaction mixture is washed with water, 1 N NaOH solution, then with water, dried over sodium sulphate and evaporated. On addition of diethyl ether 3.94 g (69%) of the above product crystallize.

M.p.: 136-138° C. $^1$H-NMR (400 MHz, CDCl$_3$): δ 1.48 (s, 9H); 2.3-2.9 (m, 3-CH$_2$), 3.69 (br, minor)+3.86 (m, major)(5-CH$_2$), 4.53 (br, 2-CH). 6.0 (br, major)+6.81 (br, minor)(NH$_2$).

d.) (2S)-4,4-difluoro-2-pyrrolidinecarboxamide Hydrochloride of the General Formula (VIII) Wherein R$^2$ and R$^3$ Mean Fluorine Atoms 3.93 g (15.7 mmol) of tert-butyl (2S)-2-(aminocarbonyl)-4,4-difluoro-1-pyrrolidinecarboxylate are dissolved in 75 ml of 25% ethanolic hydrogen chloride solution and stirred at room temperature for 4 hours. To the resulting suspension 150 ml of diethyl ether are added, the resulting white crystalline material is filtered off. 2.55 g (87%) of the above product are obtained.

M.p.: 232-233° C. $^1$H-NMR (400 MHz, DMSO-d$_6$): δ 2.43-2.51 (m, minor) and 2.81-3.05 (m, major)(3-CH$_2$), 3.71 (t, 2H, 5-CH$_2$), 4.46 (t, 1H, 2-CH), 7.81 (s, 1H,)+8.12 (s, 1H)(NH$_2$), 10.12 (br, 2H, NH$_2$$^+$).

e.) (2S)-1-(2-chloroacetyl)-4,4-difluoro-2-pyrrolidine-carboxamide of the General Formula (DC) Wherein R$^2$ and R$^3$ Mean Fluorine Atoms 2.54 g (13.6 mmol) of (2S)-4,4-difluoro-2-pyrrolidinecarboxamide hydrochloride are suspended in 25 ml of dichloromethane and to the suspension 4.1 ml (29.3 mmol) of triethylamine are added. To the resulting mixture drop wise, below −10° C. 1.2 ml (15 mmol) of chloroacetyl chloride in 20 ml of dichloromethane are added. After 1 hour of stirring the suspension is poured into 450 ml of ethyl acetate, the precipitated triethylamine hydrochloride is filtered off, the filtrate is evaporated and purified by chromatography using chloroform—methanol 4:1 mixture eluent. 3.0 g (97%) of the above product are obtained in the form of colourless oil.

$^1$H-NMR (400 MHz, DMSO-d$_6$): δ 2.34-2.52 (m, 1H)+ 2.66-2.83(m, 1H)(3-CH$_2$), 4.07-4.29 (m, 2H, 5-CH$_2$), 4.40 (qv, 2H, CH$_2$Cl), 4.71 (m, 1H, 2-CH), 7.17 (br, 1H,)+7.42 (d, 1H)(NH$_2$).

f.) (2S)-1-(2-chloroacetyly-4,4-difluoro-2-pyrrolidinecarbonitrile of the General Formula (III) Wherein R$^2$ and R$^3$ Mean Fluorine Atoms 10.4 g (46 mmol) of (2S)-1-(2-chloroacetyl)-4,4-difluoro-2-pyrrolidine-carboxamide are dissolved in 230 ml of dichloromethane and 13 ml (140 mmol) of phosphorous oxychloride are added thereto. The mixture is heated for 24 hours (if there is remaining starting material then it is refluxed further). During the refluxing the solution will become pale yellow and sticky solid material is precipitated. The solution is poured into another pot and 50 g of potassium carbonate are added thereto. After stirring for an hour the solid salts are filtered out and the solution is evaporated. Pale yellow oil is received which is triturated with n-hexane. The received yellow crystals are collected and 70 ml of diethyl-ether are added. Thus impurities are dissolved and pure white solid crystalline product is obtained. Yield: 6.0 g (56%). M.p.: 86-87° C.

$^1$H-NMR (400 MHz, CDCl$_3$): δ 2.76-2.98 (m, 2H, 3-CH$_2$), 3.92-4.26 (m, 2H, 5-CH$_2$), 4.46 (qv, 2H, CH$_2$Cl), 5.11 (m, 1H, 2-CH).

g.) (2S)-4,4-difluoro-1-(2-{[8-(2-primidinyl)-8-azabicyclo[3.2.1]oct-3-yl]exo-amino}acetyl)-2-pyrrolidinecarbonitrile 6.13 g of 8-(2-pyrimidinyl)-8-azabicyclo[3.2.1]oct-3-yl-exo-amine (30 mmol) and 5.74 g of (2S)-1-(2-chloroacetyl)-4,4-difluoro-2-pyrrolidinecarbo-nitrile (27.5 mmol) and 12.5 ml of triethylamine (90 mmol) are dissolved in 250 ml of dry acetonitrile and stirred at 70° C. for 3 hours and then at room temperature overnight. Then the mixture was evaporated to give a brownish thick oil which is purified by column chromatography using chloroform-methanol (6:1) as the eluent to result in a solid product which is crystallized from abs. ethanol. Yield: 5.7 g (77%). M.p.: 162-163° C.

$^1$H-NMR (400 MHz, DMSO-d$_6$): δ 1.32 (td, 2H), 1.6-2.0 (m, 7H), 2.6-2.9 (m, 2H), 2.85 (tt, 1H), 3.0-3.5 (m, 2H), 3.97 (ddd, 1H), 4.13 (ddd, 1H), 4.61 (m, 2H), 5.05 (dd, 1H), 6.60 (t, 1H), 8.35 (m, 2H).

Example 2

(2S,4S)-4-fluoro-1-(2-{[8-(2-pyrazinyl)-8-azabicyclo-[3.2.1]-oct-3-yl]exo-amino}acetyl)-2-pyrrolidinecarbonitrile Dihydrochloride In the general formula (I) R$^1$ means 2-pyrazinyl-group, B means a group of formula (4), R$^2$ means hydrogen atom and R$^3$ means fluorine atom.

a.) tert-butyl 8-(2-pyrazinyl)-8-azabicyclo[3.2.1]oct-3-yl-exo-carbamate with (V) General Formula— Where R$^1$ is 2-pyrazinyl, Y is COOC(CH$_3$)$_3$, B is (4) Group 0.54 ml of chloropyrazine (6 mmol) and 1.13 g of tert-butyl 8-azabicyclo[3.2.1]oct-3-yl-exo-carbamate (6 minol) 0.97 ml of 1.8-diazabicyclo [5.4.0]undec-7-ene (DBU) (6.5 mmol) are dissolved in 40 ml of 1-pentanol and heated under reflux for 50 hours. The solvents are evapotared, the residue is dissolved in 50 ml of chloroform, washed with 4×30 ml of water, dried over Na$_2$SO$_4$, and purified by column chromatography using n-hexane-ethyl acetate-chloroform (3:1:1) as eluent to result in white crystals which are triturated with n-hexane. Yield: 0.55 g (36%). M.p.: 122-123° C.

$^1$H-NMR (200 MHz, DMSO-d$_6$): δ 1.34 (s, 9H); 1.44-1.66 (m; 2H), 1.67-1.99 (m, 6H), 3.88 (m, 1H), 4.56 (bs, 2H), 6.59 (d, 1H), 7.77 (d, 1H), 8.07 (dd, 1H), 8.17 (d, 1H).

b.) 8-(2-pyrazinyl)-8-azabicyclo[3.2.1]oct-3-yl-exo-amine with (II) General Formula—Where R$^1$ and B are Given in Step 2a.)

3.85 mg of tert-butyl 8-(2-pyrimidinyl)-8-azabicyclo [3.2.1]oct-3-yl-exo-carbamate (1.26 mmol) are dissolved in 20 ml of 12% ethanolic hydrocloric acid and the solution is stirred for 7 hours. 20 ml water is added to the formed suspension and the pH is made to 11 with aqueous potassium hydroxide. The layers are separated, the organic phase are dried, evaporated and purified by column chromatography using ethyl acetate—methanol—25% aqueous NH$_3$ solution (17:3:1) as eluent to result in a pale yellow oil. Yield is 167 mg (65%). $^1$H-NMR (200 MHz, DMSO-d$_6$): δ 1.29 (t, 2H), 1.62-1.83 (m, 4H), 1.84-2.00 (m, 2H), 3.12 (sp, 1H), 4.57 (dd, 2H), 7.74 (d, 1H), 8.05 (dd, 1H), 8.15 (d, 1H).

c.) tert-butyl (2S,4S)-2-(aminocarbonyl)-4-fluoro-1-pyrrolidinecarboxylate of the General Formula (VII) Wherein $R^2$ Means Hydrogen Atom and $R^3$ Means Fluorine Atom 1.63 g (7 mmol) of (2S,4S)-1-(tert-butoxycarbonyl)-4-fluoro-2-pyrrolidinecarboxylic acid (Tetraheron Lett. 1998, 39, 1169) are dissolved in 25 ml of dichloromethane and 1.2 ml (8.4 mmol) of triethylamine are added. 0.86 ml (7 mmol) of pivaloyl chloride are added dropwise to the mixture at −15° C. and it is stirred for 1 hour and 2 ml 25% of aqueous ammonium-hydroxide solution are added thereto. After one hour of stirring the reaction mixture is washed with water, 1N sodium hydroxide solution and with water again, it is dried on sodium sulfate and evaporated. 0.88 g (54%) of the title compound is crystallized from diethylether. Melting point is 173-175° C.

$^1$H-NMR (400 MHz, DMSO-d$_6$): δ 1.38 (s, 9H); 2.07-2.25 (m, 2H, 3-CH$_2$), 3.49-3.67 (m, 2H, 5-CH$_2$), 4.13 (d, 1H, 2-CH), 5.07 and 5.35 (br, 1H, 4-H), 6.91+7.17 (br, 2H, NH$_2$).

d.) (2S,4S)-4-fluoro-2-pyrrolidinecarboxamide Hydrochloride

In the general formula (VIII) $R^2$ means hydrogen atom and $R^3$ means fluorine atom.

4 g (17.2 mmol) of tert-butyl (2S,4S)-2-(aminocarbonyl)-4-fluoro-1-pyrrolidinecarboxylate are dissolved in 75 ml of 25% ethanolic hydrogen chloride solution and it is stirred for 4 hours at room temperature. The obtained white crystalline substance is filtered off, washed with ether and dried. Thus 2.56 g (88%) of above product are obtained. M.p.: 250-251° C.

$^1$H-NMR (400 MHz, DMSO-d$_6$): δ 2.31 (t, 1H), 2.49-2.65 (m, 1H), 3.46 (m, 1H), 4.30 (dd, 1H), 5.37 (d, 1H), 7.71 (s, 1H,) and 8.09 (s, 1H)(NH$_2$), 9.7 (br, 2H, NH$_2^+$).

e.) (2S,4S)-1-(2-chloroacetyl)-4-fluoro-2-pyrrolidinecarboxamide

In the general formula (IX) $R^2$ means hydrogen atom and $R^3$ means fluorine atom.

2.54 g (15 mmol) of (2S,4S)-4-fluoro-2-pyrrolidinecarboxamide hydrochloride are suspended in 60 ml of dichloromethane and 4.6 ml (33 mmol) of triethylamine are added thereto. To the obtained mixture, 1.27 ml (16 mmol) of chloroacetyl chloride dissolved in 15 ml of dichloromethane are added dropwise below −10° C. The reaction mixture is stirred for an hour and the suspension is poured into 500 ml of ethylacetate, the precipitated triethylamine hydrochloride is filtered off, the filtrate is concentrated and purified by chromatography using a chloroform-methanol 4:1 mixture.

Thus 3.0 g (97%) of title compound are obtained as a colourless oil which crystallizes during standing. Its melting point is 95-96° C.

$^1$H-NMR (400 MHz, DMSO-d$_6$): δ 2.22-2.50 (m, 2H, 3-CH$_2$), 3.57-4.04 (m, 2H, 5-CH$_2$), 4.36 (qv, 2H, CH$_2$Cl), 5.22 (d, 0.5H) and 5.39 (d, 0.5H)(4-CH), 7.03 (s, 0.74H) and 7.22 (s, 1H) and 7.56 (s, 0.26H)(NH$_2$).

f.) (2S,4S)-(2-chloroacetyl)-4-fluoro-2-pyrrolidinecarbonitrile

In the general formula (III) $R^2$ means hydrogen atom and $R^3$ means fluorine atom.

1.73 g (46 mmol) of (2S,4S)-1-(2-chloroacetyl)-4-fluoro-2-pyrrolidinecarboxamide are dissolved in a mixture of 20 ml of dry acetonitrile and 30 ml of dry dichloromethane and 32 ml (25 mmol) of phosphorous oxychloride are added thereto. The mixture is refluxed for 24 hours. The solution is poured into another flask and 50 g of potassium carbonate are added and the mixture is stirred for an hour. Solid salts are filtered off and after evaporation of the filtrate a pale yellow oil is obtained which is purified by chromatography using a 9:1 mixture of chloroform and methanol. The pure above product is 0.6 g (43%) white crystalline solid. M.p.: 134-136° C.

$^1$H-NMR (400 MHz, CDCl$_3$): δ 2.23-2.62 (m, 2H, 3-CH$_2$), 3.59-4.06 (m, 2H, 5-CH$_2$), 4.46 (qv, 2H, CH$_2$Cl), 4.99 (m, 1H, 2-CH), 5.36(m, 0,5H) and 5.64 (m, 0,5H)(4-H).

g.) (2S,4S-4-fluoro-1-(2-{[8-(2-pyrazinyl)-8-azabicyclo[3.2.1]octan-3-yl]exoamino}acetyl-2-pyrrolidinecarbonitrile Dihydrochloride _of general formula (1) wherein $R^1$ means 2-pyrazinyl group, B means a group of formula (4), $R^2$ stands for hydrogen atom and $R^3$ stands for fluorine atom.

243 mg (1.2 mmol) of 8-(2-pyrazinyl)-8-azabicyclo[3.2.1]oct-3-yl-exo-amine reacted with 191 mg (1 mmol) of (2S,4S)-1-(2-chloroacetyl)-4-fluoro-2-pyrrolidine carbonitrile as it is described in Example 1/g.). The product is purified by chromatography using a 4:1 mixture of chloroform and methanol and its dihydrochloride is prepared. Thus 125 mg (29%) of title compound are obtained in the form of white crystals. M.p.: 201-202° C. $^1$H-NMR (400 MHz, DMSO-d$_6$): δ 1.76-1.80 (m, 4H), 1.94-2.01 (m, 4H), 2.47-2.51 (m, 2H), 3.64-3.80 (m, 1H), 3.79-4.03(m, 2H), 4.15 (m, 1H), 4.67 (m, 2H), 5.03 (m, 1H), 5.52 (d, 1H), 7.86 (s, 1H), 8.15 (dd, 1H), 8.28 (d, 2H), 8.90 and 9.00 (s, 2H).

Example 3

(2S)-4,4-Difluoro-1-(2-{[1-(2-pyrazinyl)piperidin-4-yl]amino}acetyl)-2-pyrrolidine Carbonitrile Dihydrochloride The meaning of $R^1$ is 2-pyrazinyl group, B means a group of formula (1), $R^2$ and $R^3$ mean fluorine atom in general formula (I).

a.) 1-(2-Pyrazinyl)-4-acetamino-piperidine with (V) General Formula—Where $R^1$ is 2-pyrazinyl, Y is COCH$_3$, B is (1) Group 0.45 ml of chloropyrazine (5 mmol) and 1.6 g of 4-acetaminopyperidine (10 mmol) are dissolved in 15 ml of 1-pentanol and heated under reflux for 14 hours. The solvent are evaporated and the residue is purified by column chromatography using ethyl acetate—methanol—25% aqueous NH$_3$ solution (17:3:1) as eluent to result 0.81 g (76%) of the above crystalline product. M.p.: 158-160° C. $^1$H-NMR (200 MHz, DMSO-d$_6$): δ 1.34 (dq, 2H), 1.78 (m, 5H), 3.03 (dt, 2H), 3.74-3.89 (m,1H), 4.21 (td, 2H), 7.77 (d, 1H, 3'-H), 7.80 (s, 1H, NH), 8.05 (dd, 1H, 5'-H), 8.31 (d, 1H, 6'-H).

b.) 1-(2-Pyrazinyl-4-amino-piperidine with (II) General Formula—Where $R^1$ and B are Given in Step 3a.)

697 mg of 1-(2-Pyrazinyl)-4-acetamino-piperidine (3.2 mmol) are dissolved in 15 ml of 2 N hydrochloric acid and the solution is heated under reflux for 8 hours. After cooling the mixture is treated with 20% sodium hydroxide and the aqueous solution washed with 4×20 ml dichloromethane. The combined organic layers are dried over $Na_2SO_4$ and evaporated to afford 292 mg (52%) of the above product as yellow crystals.

M.p.: 113-115° C.

$^1$H-NMR (200 MHz, DMSO-$d_6$—$CDCl_3$): δ 1.09-1.36 (m, 2H), 1.78 (d, 2H), 2.78-3.31 (m, 4H), 3.54 (m, 1H), 7.76 (d, 1H, 3'-H), 8.03 (dd, 1H, 5'-H), 8.29 (d, 1H, 6'-H).

c.) (2S)-4,4-Difluoro-1-(2-{[1-(2-pyrazinyl)piperidin-4-yl]amino}acetyl)-2-pyrrolidinecarbonitrile Dihydrochloride of General Formula (I) Wherein $R^1$ is 2-pyrazinyl Group, B Means a Group of Formula (1), $R^2$ and $R^3$ Mean Fluorine Atom 63 mg of 1-(2-pyrazinyl)-4-amino-piperidine (0.32 mmol) and 62 mg (2S)-1-(2-chloroacetyl)-4,4-difluoro-2-pyrrolidine carbonitrile (0.32 mmol) and 285 mg of polymer-bound 2-tert-butylimino-2-diethylamino-1,3-dimethylperhydro-1,3,2-diazaphosphorine (PBEMP) (0.73 mmol) are dissolved in 20 ml dry acetonitrile and stirred at 55° C. for 8 hours. The resin is removed by filtration, the filtrate is concentrated by vacuum and the residue is purified by column chromatography using chloroform—methanol (9:1) as eluent to result an oil, which is treated with hydrochloric acid in diethylether result in 83 mg (60%) of title compound, as white crystals. M.p.: 158-160° C. $^1$H-NMR (400 MHz, DMSO-$d_6$): δ 1.54 (m, 2H), 2.15 (m, 2H), 2.80-2.95 (m, 4H), 4.20-4.25 (m, 4H), 4.55 (d, 2H,), 5.20 (t, 1H), 7.00 (d, 1H), 7.87 (dd, 1H), 8.50 (d, 1H); 9.38 (br, 2H).

Example 4

(2S)-4,4-Difluoro-1-(2-{[1-(5-cyanopyridin-2-yl)piperidin-4-yl]amino}acetyl)-2-pyrrolidine Carbonitrile Dihydrochloride The meaning of $R^1$ is 5-cyano-pyridin-2-yl group, B means a group of formula (1), $R^2$ and $R^3$ Mean Fluorine Atom in General Formula (I).

a.) 1-(5-Cyanopyridin-2-yl)-4-acetamino-piperidine with (V) General Formula—Where $R^1$ is 5-cyanopyridin-2-yl, Y is $COCH_3$, B is (1) Group Following procedures outlined for examples 3a), the above crystalline product is isolated. Melting point is 246-251° C. $^1$H-NMR (200 MHz, DMSO-$d_6$): δ 1.19-1.39 (m, 2H), 1.82 (m, 5H), 3.04-3.18 (m, 2H), 3.85 (m, 1H), 4.29 (dd, 2H), 6.94 (d, 1H), 7.82 (dd, 1H), 8.46 (d, 1H).

b.) 1-(5-Cyanopyridin-2-yl)-4-amino-piperidine with (II) General Formula—where $R^1$ and B are Given in Step 4a.)

Following procedures outlined for examples 3b), the above crystalline product is isolated. M.p.: 65-68° C. $^1$H-NMR (200 MHz, $CDCl_3$-DMSO-$d_6$): δ 1.16-1.38 (m, 2H), 1.83-1.92 (m, 2H), 2.89-3.06 (m, 2H), 4.26 (dd, 2H), 6.54 (d, 1H), 7.50 (dd, 1H), 8.29 (d, 1H).

c.) (2S)-4,4-Difluoro-1-(2-{[1-(5-cyanopyridin-2-yl)piperidin-4-yl]amino}acetyl)-2-pyrrolidinecarbonitrile Dihydrochloride Following procedures outlined for examples 3c), the above crystalline product is isolated. M.p.: 146-147° C. $^1$H-NMR (DMSO-$d_6$): δ 1.56 (m, 2H), 2.15 (d, 2H), 2.92 (m, 4H), 4.20 (m, 4H), 4.55 (d, 2H), 5.20 (t, 2H), 7.01 (d, 1H), 7.88 (d, 1H), 8.49 (dd, 1H), 9.38 (d, 2H).

Following procedures, outlined for Examples 1-2, the compounds listed in the Table 1 were prepared as a free base or as a salt.

TABLE 1

(I)

| Example | $R^1$ | B (Formula) | $R^2$ | $R^3$ | Melting point, composition, physical appearance |
|---------|-------|-------------|-------|-------|-------------------------------------------------|
| 5. | pyridin-2-yl | (4) | F | F | 133-141° C., dihydrochloride, off-white crystals |
| 6. | pyrazin-2-yl | (4) | F | F | 238-240° C., dihydrochloride, yellow crystals |

TABLE 1-continued (I) Structure: R¹—B—NH—CH₂—C(=O)—N(pyrrolidine with R², R³ at 4-position and CN at 2-position)

| Example | R¹ | B (Formula) | R² | R³ | Melting point, composition, physical appearance |
|---|---|---|---|---|---|
| 7. | 5-cyano-2-methylpyridin-yl (NC-pyridine-CH₃) | (4) | F | F | 237-239° C., dihydrochloride, white crystals |
| 8. | 5-nitro-2-methylpyridin-yl (O₂N-pyridine-CH₃) | (4) | F | F | 160-162° C., yellow crystals |
| 9. | 6-chloro-2-methylpyridin-yl (Cl-pyridine-CH₃) | (4) | F | F | 119-121° C., dihydrochloride, white crystals |
| 10. | 4-methyl-2-methylpyridin-yl (H₃C-pyridine-CH₃) | (4) | F | F | 221-225° C., trihydrochloride, white crystals |
| 11. | 5-bromo-2-methylpyridin-yl (Br-pyridine-CH₃) | (4) | F | F | 200-201° C., dihydrochloride, white crystals |
| 12. | 6-methyl-2-methyl-3-cyanopyridin-yl (H₃C-pyridine-CH₃, CN) | (4) | F | F | 185-189° C., dihydrochloride, white crystals |
| 13. | 6-cyano-3-methylpyridazin-yl (NC-pyridazine-CH₃) | (4) | F | F | 108-110° C., white crystals |
| 14. | 6-chloro-3-methylpyridazin-yl (Cl-pyridazine-CH₃) | (4) | F | F | >340° C., dihydrochloride, off-white crystals |
| 15. | 4-chloro-2-methylpyrimidin-yl (Cl-pyrimidine-CH₃) | (4) | F | F | 300-305° C., dihydrochloride white crystals |
| 16. | 5-chloro-2-methylpyrazin-yl (Cl-pyrazine-CH₃) | (4) | F | F | 185-186° C., dihydrochloride, yellow crystals |

TABLE 1-continued (I)

| Example | R¹ | B (Formula) | R² | R³ | Melting point, composition, physical appearance |
|---|---|---|---|---|---|
| 17. | 2-chloro-4-methylpyrimidin-yl | (4) | F | F | 293-296° C., dihydrochloride, white crystals |
| 18. | 6-chloro-4-methylpyrimidin-yl | (4) | F | F | 148-167° C., dihydrochloride, white solid |
| 19. | 5-cyanopyrazin-2-yl | (4) | F | F | >350° C., 1,5 HCl, white crystals |
| 20. | 2-methylthio-4-methylpyrimidin-yl | (4) | F | F | 240-243° C., dihydrochloride, white crystals |
| 21. | 2-methylthiazol-yl | (4) | F | F | 102-104° C., white crystals |
| 22. | quinolin-2-yl | (4) | F | F | 236-241° C., trihydrochloride, white crystals |
| 23. | quinoxalin-2-yl | (4) | F | F | 201-202° C., dihydrochloride, white crystals |
| 24. | benzothiazol-2-yl | (4) | F | F | 256-259° C., dihydrochloride, white crystals |
| 25. | benzoxazol-2-yl | (4) | F | F | 119-120° C., yellow crystals |
| 26. | (E)-4-(1,3-benzodioxol-5-yl)-3-buten-2-on-yl | (4) | F | F | 114-117° C., white solid |

TABLE 1-continued (I)

| Example | R¹ | B (Formula) | R² | R³ | Melting point, composition, physical appearance |
|---|---|---|---|---|---|
| 27. | (E)-4-phenyl-3-buten-2-on-1-yl (cinnamoylmethyl) | (4) | F | F | 94-97° C., white solid |
| 28. | 6-methyl-pyridine-3-carbonitrile (5-cyano-2-methylpyridin-2-yl) | (2) | F | F | 66-70° C., white foam |
| 29. | 6-methyl-pyridine-3-carbonitrile | (3) | F | F | 216-218° C., dihydrochloride, white crystals |
| 30. | 2-methylpyrimidine | (5) | F | F | 182-185° C., white solid |
| 31. | 2-methylpyrazine | (5) | F | F | 241-243° C., trihydrochloride, yellow crystals |
| 32. | 2-methylpyrazine | (6) | F | F | 276-278° C., dihydrochloride, yellow crystals |
| 33. | 6-methyl-pyridine-3-carbonitrile | (6) | F | F | 240-243° C., dihydrochloride, yellow crystals |
| 34. | 2-methylbenzoxazole | (6) | F | F | 82-85° C., hydrochlorid, off-white crytals |
| 35. | 2-methylpyrimidine | (7) | F | F | 141-144° C., white crystals |
| 36. | 6-methyl-pyridine-3-carbonitrile | (7) | F | F | 281-284° C., dihydrochloride, yellow crystals |

TABLE 1-continued

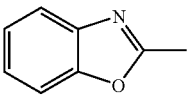

| Example | R¹ | B (Formula) | R² | R³ | Melting point, composition, physical appearance |
|---|---|---|---|---|---|
| 37. | (benzoxazol-2-yl) | (7) | F | F | 271-272° C., dihydrochloride, off-white crytals |

Following procedures, outlined for Examples 3-4, the compounds listed in the Table 2 were prepared as a free base or as a salt.

TABLE 2

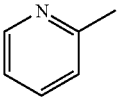

| Example | R¹ | B (Formula) | R² | R³ | Melting point, composition, physical appearance |
|---|---|---|---|---|---|
| 38. | (pyridin-2-yl) | (1) | F | F | 219-228° C., dihydrochloride, white crystals |
| 39. | (pyrimidin-2-yl) | (1) | F | F | 198-200° C., dihydrochloride, white crystals |
| 40. | (pyrimidin-4-yl) | (1) | F | F | 224-229° C., trihydrochloride, off white crystals |
| 41. | (pyrazin-2-yl) | (1) | H | F | 157-158° C., pale yellow crystals |
| 42. | (5-methylpyridin-2-yl) | (1) | F | F | 2,5 HCl, amorphous white solid |
| 43. | (4-methylpyridin-2-yl) | (1) | F | F | 292-295° C., dihydrochloride, white crystals |

TABLE 2-continued (I)

| Example | R¹ | B (Formula) | R² | R³ | Melting point, composition, physical appearance |
|---|---|---|---|---|---|
| 44. | 6-chloro-2-methylpyridin-3-yl | (1) | F | F | 210-212° C., dihydrochloride, white crystals |
| 45. | 5-chloro-2-methylpyridin-3-yl | (1) | F | F | 284-288° C., dihydrochloride, white crystals |
| 46. | 5-bromo-2-methylpyridin-3-yl | (1) | F | F | 282-285° C., dihydrochloride, off white crystals |
| 47. | 2-methyl-5-nitropyridin-3-yl | (1) | F | F | 170-173° C., dihydrochloride, yellow crystals |
| 48. | 5-cyano-2-methylpyridin-3-yl | (1) | H | F | 122-124° C., white crystals |
| 49. | 3-cyano-2,6-dimethylpyridin-5-yl | (1) | F | F | 102-105° C., dihydrochloride, white crystals |
| 50. | 6-cyano-3-methylpyridazin-4-yl | (1) | F | F | 63-65° C., white crystals |
| 51. | 6-chloro-3-methylpyridazin-4-yl | (1) | F | F | >350° C., dihydrochloride, white crystals |
| 52. | 4-chloro-2-methylpyrimidin-5-yl | (1) | F | F | 168-171° C., dihydrochloride, white crystals |
| 53. | 5-chloro-3-methylpyrazin-2-yl | (1) | F | F | 173-175° C., dihydrochloride, yellow crystals |

TABLE 2-continued (I)

| Example | R¹ | B (Formula) | R² | R³ | Melting point, composition, physical appearance |
|---|---|---|---|---|---|
| 54. | 2-chloro-4-methylpyrimidin-4-yl | (1) | F | F | 162-163° C., dihydrochloride, white crystals |
| 55. | 6-chloro-4-methylpyrimidin-4-yl | (1) | F | F | Dihydrochloride, amorphous off-white solid |
| 56. | 5-cyano-2-methylpyrazin-2-yl | (1) | F | F | 51-53° C., light yellow foam |
| 57. | 2-methylthio-4-methylpyrimidin-4-yl | (1) | F | F | 228-230° C., dihydrochloride, white crystals |
| 58. | 2-methylthiazol-2-yl | (1) | F | F | 281-284° C., dihydrochloride, yellow crystals |
| 59. | 1-methyl-5-methyl-4-nitroimidazolyl | (1) | F | F | 116-120° C., dihydrochloride, yellow crystals |
| 60. | 2-methylquinolin-2-yl | (1) | F | F | 178-185° C., salt formed with 2.5 molecules of HCl, white crystals |
| 61. | 6-fluoro-2-methylquinolin-2-yl | (1) | F | F | Dihydrochloride, amorphous off-white solid |
| 62. | 2,4-dimethylquinolin-2-yl | (1) | F | F | 226-235° C., dihydrochloride, white crystals |
| 63. | 1-methylisoquinolin-1-yl | (1) | F | F | 278-283° C., dihydrochloride, off-white crystals |

TABLE 2-continued (I) Structure: R¹—B—NH—CH₂—C(O)—N(pyrrolidine with R², R³ at 4-position and CN at 2-position)

| Example | R¹ | B (Formula) | R² | R³ | Melting point, composition, physical appearance |
|---|---|---|---|---|---|
| 64. | 3-methylquinoxalin-2-yl | (1) | F | F | 2,5 HCl, amorphous yellow solid |
| 65. | 2-methylbenzothiazol-yl | (1) | F | F | 318-320° C., dihydrochloride, white crystals |
| 66. | 2-methylbenzoxazol-yl | (1) | F | F | 157-160° C., white crystals |

Following procedures, outlined for Examples 1-4, the compounds of the general formula (I) listed in the Table 3 were prepared as a free base or as a salt.

TABLE 3

(I)

| Example | R¹ | B (Formula) | R² | R³ | Melting point, composition, physical appearance |
|---|---|---|---|---|---|
| 67. | 5-amino-2-methylpyridin-yl | (1) | F | F | 216-228° C., trihydrochloride, off white crystals |
| 68. | 3-methyl-6-phenylpyridazin-yl | (1) | F | F | 163-167° C., cream-coloured solid |

TABLE 3-continued (I) structure: R¹—B—NH—CH₂—C(=O)—N(pyrrolidine with R², R³ at 4-position and CN at 2-position)

| Example | R¹ | B (Formula) | R² | R³ | Melting point, composition, physical appearance |
|---|---|---|---|---|---|
| 69. | 1-phenyl-tetrazol-5-yl | (1) | F | F | dihydrochloride, amorphous off-white solid |
| 70. | 4,6-dimethoxy-1,3,5-triazin-2-yl (MeO, OMe) | (1) | F | F | 275-277° C., dihydrochloride, white solid |
| 71. | 1-phenyl-tetrazol-5-yl | (4) | F | F | 148-152° C., dihydrochloride, pale yellow crystals |
| 72. | benzyl (phenyl-CH₂-) | (7) | F | F | 229-231° C., trihydrochloride, white crystals |

Following procedures outlined for Examples 1a) and 2a) the intermediate compounds of the general formula (V) listed in the Table 4 were prepared.

TABLE 4

(V) structure: R¹—N(bicyclic)—NH—C(=O)—O—C(CH₃)₃

| Example | R¹ | Characterisation (M.p., LC/MS or aromatic protons by ¹H-NMR [DMSO-d₆] |
|---|---|---|
| 4.1. | pyridin-2-yl | 6.93(m, 1H), 7.35(m, 1H), 7.98(m, 1H), 8.04(d, 1H) |

TABLE 4-continued (V)

| Example | R¹ | Characterisation (M.p., LC/MS or aromatic protons by ¹H-NMR [DMSO-d₆] |
|---|---|---|
| 4.2. | 6-methyl-3-cyanopyridin-2-yl (NC-pyridine-CH₃) | 141-143° C. |
| 4.3. | 6-methyl-3-nitropyridin-2-yl (O₂N-pyridine-CH₃) | 212-215° C. |
| 4.4. | 6-chloro-2-methylpyridin-3-yl (Cl-pyridine-CH₃) | 6.58(d, 1H), 6.65(d, 1H), 7.51(t, 1H) |
| 4.5. | 4-methyl-pyridin-2-yl (H₃C-pyridine) | 2.37(s, 3H), 6.75(1H, d), 7.15(1H, dd), 7.81(1H, d) |
| 4.6. | 5-bromo-2-methylpyridin-... (Br-pyridine-CH₃) | 6.75(d, 1H), 7.60(d, 1H), 8.12(s, 1H) |
| 4.7. | 6-methyl-2-methyl-3-cyanopyridin-... (H₃C-pyridine-CH₃, CN) | 6.65(d, 1H), 7.84(d, 1H) |
| 4.8. | 6-cyanopyridazin-3-yl (NC-pyridazine-CH₃) | 227-230° C. |
| 4.9. | 6-chloropyridazin-3-yl (Cl-pyridazine-CH₃) | 7.30(d, 1H), 7.51(d, 1H) |
| 4.10. | 4-chloro-2-methylpyrimidin-... (Cl-pyrimidine-CH₃) | 6.71(d, 1H), 8.31(d, 1H) |
| 4.11. | 5-chloro-...-pyrazin-... (Cl-pyrazine-CH₃) | 161-162° C. |
| 4.12. | 2-chloro-...-pyrimidin-... (Cl-pyrimidine-CH₃) | 6.72(d, 1H), 8.04(d, 1H) |

TABLE 4-continued
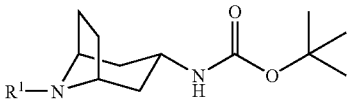
(V)
| Example | R¹ | Characterisation (M.p., LC/MS or aromatic protons by ¹H-NMR [DMSO-d₆] |
|---|---|---|
| 4.13. | 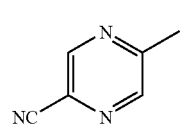 | 187-188° C. |
| 4.14. | 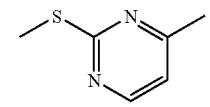 | [MH]⁺ = 330 |
| 4.15. | 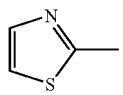 | 172-174° C. |
| 4.16. | 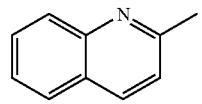 | 6.80(d, 1H), 7.19(d, 1H) |
| 4.17. | 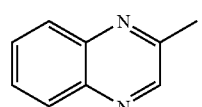 | 6.87(d, 1H), 7.20(td, 1H), 7.61(m, 1H), 7.57(m, 2H), 7.86(d, 1H) |
| 4.18. | 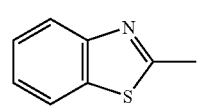 | 7.38(td, 1H), 7.57(td, 1H), 7.74(dd, 1H), 7.88(dd, 1H), 8.45(s, 1H) |
| 4.19. | 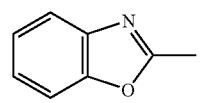 | 7.16(t, 1H), 7.35(t, 1H), 7.53(d, 1H), 7.86 (d, 1H) |
| 4.20. | 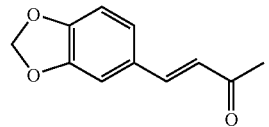 | 163-165° C. |
| 4.21. | 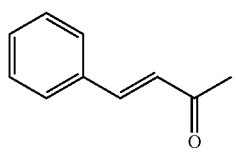 | 166-169° C. |
| 4.22. |  | 153-156° C. |

TABLE 4-continued (V) structure: R¹—N[bicyclic]—NH—C(=O)—O—C(CH₃)₃

| Example | R¹ | Characterisation (M.p., LC/MS or aromatic protons by ¹H-NMR [DMSO-d₆] |
|---|---|---|
| 4.23. | 1-phenyl-5-methyl-tetrazol-yl | 7.51(m, 5H) |

Following procedures outlined for Examples 1a) and 2a) the intermediate compounds of the general formula (V) listed in the Table 5 were prepared.

TABLE 5

(V) structure: R¹—B—NH—C(=O)—O—C(CH₃)₃

| Example | R¹ | B (Formula) | Characterisation (M.p. or aromatic protons by ¹H-NMR [DMSO-d₆] |
|---|---|---|---|
| 5.1. | 5-cyano-pyridin-2-yl | (2) | 154-156° C. |
| 5.2. | pyrimidin-2-yl | (5) | 134-135° C. |
| 5.3. | pyrazin-2-yl | (5) | 159-161° C. |
| 5.4. | pyrazin-2-yl | (6) | 7.82(d, 1H), 8.11(d, 1H), 8.35(s, 1H) |
| 5.5. | 5-cyano-pyridin-2-yl | (6) | 6.93(d, 1H), 7.91(d, 1H), 8.54(s, 1H) |
| 5.6. | benzoxazol-2-yl | (6) | 6.99(t, 1H), 7.13(t, 1H), 7.26(d, 1H), 7.36(d, 1H) |

TABLE 5-continued

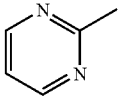
(V)

| Example | R¹ | B (Formula) | Characterisation (M.p. or aromatic protons by ¹H-NMR [DMSO-d₆] |
|---|---|---|---|
| 5.7. | 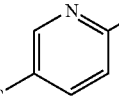 | (7) | 6.50(t, 1H), 8.33(m, 2H) |
| 5.8. | 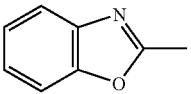 | (7) | 6.90(d, 1H), 7.80(d, 1H), 8.44(s, 1H) |
| 5.9. | 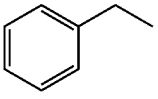 | (7) | 6.98(t, 1H), 7.12(t, 1H), 7.29(d, 1H), 7.39(d, 1H) |
| 5.10. | 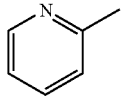 | (7) | 176-176° C. |

Following procedures outlined for Examples 3a) and -4a) the intermediate compounds of the general formula (V) listed in the Table 6. were prepared (Y=Ac(acetyl) or Boc=tert butyloxy-carbonyl).

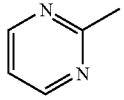
(V)

| Example | R¹ | Y | Characterisation (M.p., LC/MS or aromatic protons by ¹H-NMR [DMSO-d₆]) |
|---|---|---|---|
| 6.1. | 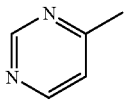 | Ac | 6.60(dd, 1H), 6.67(d, 1H), 7.48(td, 1H), 8.17(dd, 1H) |
| 6.2. | 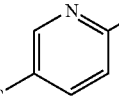 | Boc | 127-129° C. |
| 6.3. | 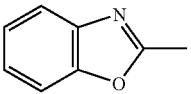 | Boc | 138-140° C. |
| 6.4. | 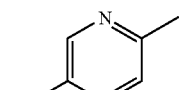 | Ac | 2.12(s, 3H), 6.74(d, 1H), 7.33(dd, 1H), 7.76(d, 1H) |

-continued (V)

R¹—N⟨piperidine⟩N(H)—Y

| Example | R¹ | Y | Characterisation (M.p., LC/MS or aromatic protons by ¹H-NMR [DMSO-d₆]) |
|---|---|---|---|
| 6.5. | 4-methyl-2-pyridyl (H₃C on pyridine) | Ac | 166-164° C. |
| 6.6. | 6-chloro-2-pyridyl (Cl on pyridine) | Boc | 6.58(d, 1H), 6.65(d, 1H), 7.51(t, 1H) |
| 6.7. | 5-chloro-2-pyridyl | Ac | 6.65(d, 1H), 7.45(dd, 1H), 8.10(d, 1H) |
| 6.8. | 5-bromo-2-pyridyl | Ac | 6.72(d, 1H), 7.60(d, 1H), 8.13(s, 1H) |
| 6.9. | 5-nitro-2-pyridyl (O₂N on pyridine) | Ac | 223-226° C. |
| 6.10. | 6-methyl-3-cyano-2-pyridyl (H₃C, CN on pyridine) | Boc | 139-140° C. |
| 6.11. | 6-cyano-3-pyridazinyl (NC on pyridazine) | Ac | 126-128° C. |
| 6.12. | 6-chloro-3-pyridazinyl (Cl on pyridazine) | Boc | 6.95(d, 1H), 7.22(d, 1H) |
| 6.13. | 4-chloro-2-pyrimidinyl (Cl on pyrimidine) | Boc | 169-171° C. |
| 6.14. | 5-chloro-...pyrimidinyl (Cl on pyrimidine) | Boc | 144-146° C. |
| 6.15. | 2-chloro-4-pyrimidinyl (Cl on pyrimidine) | Boc | 172-174° C. |
| 6.16. | 6-chloro-4-pyrimidinyl (Cl on pyrimidine) | Boc | 149-152° C. |

-continued $$\text{R}^1-\text{N}\underset{}{\bigcirc}\text{N}-\text{Y} \quad (V)$$
$$\phantom{R^1-N}\phantom{\bigcirc}\text{H}$$

| Example | R¹ | Y | Characterisation (M.p., LC/MS or aromatic protons by ¹H-NMR [DMSO-d₆]) |
|---|---|---|---|
| 6.17. | 5-cyanopyrazin-2-yl | Boc | [MH]⁺ = 304 |
| 6.18. | 2-(methylthio)-4-pyrimidinyl | Ac | 196-200° C. |
| 6.19. | thiazol-2-yl | Ac | 6.80(d, 1H), 7.12(d, 1H) |
| 6.20. | 1-methyl-5-nitro-imidazol-2-yl | Ac | 234-236° C. |
| 6.21. | quinolin-2-yl | Ac | 163-166° C. |
| 6.22. | 6-fluoroquinolin-2-yl | Boc | 7.59(m, 3H), 8.10(m, 1H), 8.29(d, 1H) |
| 6.23. | 4-methylquinolin-2-yl | Boc | 129-133° C. |
| 6.24. | isoquinolin-1-yl | Boc | 7.49(d, 1H), 7.72(td, 1H), 7.85(td, 1H), 7.90(t, 1H), 7.98(d, 1H), 8.13(d, 1H) |
| 6.25. | quinoxalin-2-yl | Boc | 7.38(td, 1H), 7.57(td, 1H), 7.74(dd, 1H), 7.88(dd, 1H), 8.45(s, 1H) |
| 6.26. | benzothiazol-2-yl | Ac | 7.01(t, 1H), 7.27(t, 1H), 7.42(d, 1H), 7.73(d, 1H) |
| 6.27. | benzoxazol-2-yl | Boc | 165-166° C. |

-continued (V)

R¹—N⟨ ⟩N—Y
           H

| Example | R¹ | Y | Characterisation (M.p., LC/MS or aromatic protons by ¹H-NMR [DMSO-d₆]) |
|---|---|---|---|
| 6.28. | 3-methyl-6-phenylpyridazin-yl | Boc | 206-211° C. |
| 6.29. | 1-phenyl-5-methyltetrazol-yl | Boc | 7.5(m, 5H) |
| 6.30. | 2,4-dimethoxy-6-methyl-1,3,5-triazinyl (MeO, OMe) | Boc | 159-160° C. |

Following procedures outlined for Examples 1b) and 2b) the intermediate compounds of the general formula (II) listed in the Table 7. were prepared.

TABLE 7

(II)

R¹—N⟨ ⟩NH₂

| Example | R¹ | Characterisation (M.p. or aromatic protons by ¹H-NMR [DMSO-d₆]) |
|---|---|---|
| 7.1. | 6-methylpyridin-2-yl | 6.96(m, 1H), 7.34(m, 1H), 8.02(m, 1H), 8.08(d, 1H) |
| 7.2. | 5-cyano-6-methylpyridin-2-yl (NC) | 123-125° C. |
| 7.3. | 5-nitro-6-methylpyridin-2-yl (O₂N) | 175-178° C. |
| 7.4. | 6-chloro-pyridin-2-yl (Cl) | 6.55(d, 1H), 6.63(d, 1H), 7.49(t, 1H) |

TABLE 7-continued
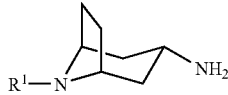
(II)
| Example | R¹ | Characterisation (M.p. or aromatic protons by ¹H-NMR [DMSO-d₆]) |
|---|---|---|
| 7.5. | 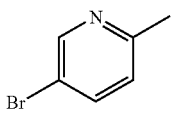 | 2.40(s, 3H), 6.82(dd, 1H,), 7.20(d, 1H), 7.89(d, 1H) |
| 7.6. | 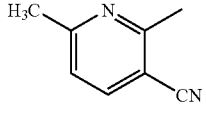 | 6.40(d, 1H), 7.60(d, 1H), 8.14(s, 1H) |
| 7.7. | 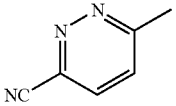 | 2.35(s, 3H), 6.62(d, 1H), 7.81(d, 1H) |
| 7.8. | 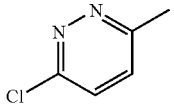 | 120-123° C. |
| 7.9 | 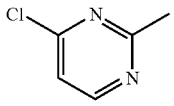 | 7.32(d, 1H), 7.58(d, 1H), |
| 7.10. | 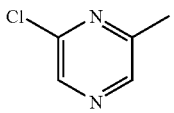 | 6.68(d, 1H), 8.29(d, 1H) |
| 7.11. | 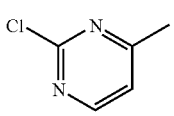 | 7.77(s, 1H), 8.13(s, 1H) |
| 7.12. | 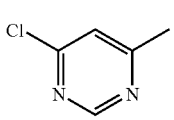 | 6.69(d, 1H), 8.02(d, 1H) |
| 7.13. | 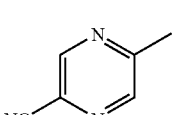 | 194-198° C. |
| 7.14. | 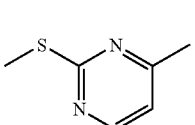 | 115-117° C. |
| 7.15. |  | 2.40(s, 3H), 6.40(d, 1H), 7.87(d, 1H) |

TABLE 7-continued
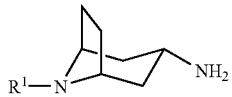
(II)
| Example | R¹ | Characterisation (M.p. or aromatic protons by ¹H-NMR [DMSO-d₆]) |
|---|---|---|
| 7.16. | 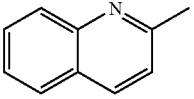 | 6.79(d, 1H), 7.12(d, 1H) |
| 7.17 | 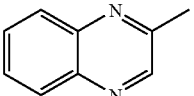 | 6.86(d, 1H), 7.19(td, 1H), 7.52(m, 2H), 7.69(dd, 1H), 7.84(d, 1H) |
| 7.18 | 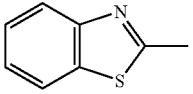 | 7.35(m, 1H), 7.58(m, 1H,), 7.80(dd, 1H), 8.66(s, 1H) |
| 7.19 | 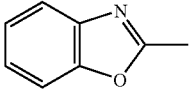 | 126-127° C. |
| 7.20. | 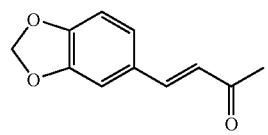 | 127-129° C. |
| 7.21. | 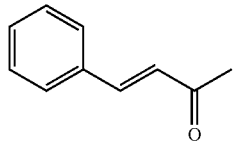 | 90-93° C. |
| 7.22 | 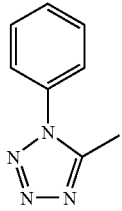 | 107-107° C. |
| 7.23. | | 227-228° C. as dihydrochloride |

Following procedures outlined for Examples 1b) and 2b) the intermediate compounds of the general formula (II) listed in the Table 8 were prepared.
TABLE 8
R¹—B—NH₂ (II)
| Example | R¹ | B (Formula) | Characterisation (M.p. or aromatic protons by ¹H-NMR [DMSO-d₆]) |
|---|---|---|---|
| 8.1. | 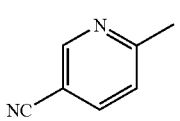 | (2) | 6.49(d, 1H), 7.76(dd, 1H), 8.43(d, 1H) |
| 8.2. | 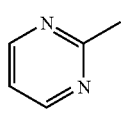 | (5) | 85-89° C. |
| 8.3. | 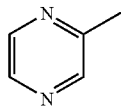 | (5) | 7.74(d, 1H), 8.04(d, 1H), 8.15(s, 1H) |
| 8.4. | 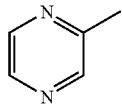 | (6) | 7.80(d, 1H), 8.12(d, 1H), 8.37(s, 1H) |
| 8.5. | 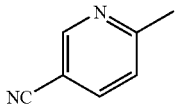 | (6) | 6.95(d, 1H), 7.89(d, 1H), 8.51(s, 1H) |
| 8.6. | 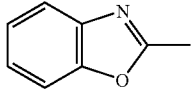 | (6) | 7.00(t, 1H), 7.14(t, 1H), 7.26(d, 1H), 7.37(d, 1H) |
| 8.7. | 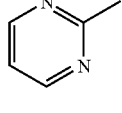 | (7) | 6.50(t, 1H), 8.29(d, 1H), 8.31(d, 1H) |
| 8.8. | 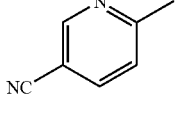 | (7) | 6.90(d, 1H), 7.80(d, 1H), 8.47(s, 1H) |
| 8.9. | 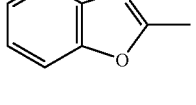 | (7) | 6.95(t, 1H), 7.14(t, 1H), 7.26(d, 1H), 7.37(d, 1H) |
| 8.10. | 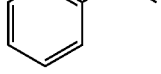 | (7) | 3.83(s, 2H), 7.21-7.40(, m, 5H) |

Following procedures outlined for Examples 3b) and 4b) the intermediate compounds of the general formula (II) listed in the Table 9. were prepared.
TABLE 9
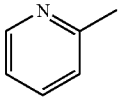
(II)
| Example | R¹ | Characterisation (M.p., LC/MS or aromatic protons by ¹H-NMR [DMSO-d₆]) |
|---|---|---|
| 9.1. | 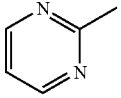 | 6.55(dd, 1H), 6.79(d, 1H,), 7.48(td, 1H), 8.07 (dd, 1H) |
| 9.2. | 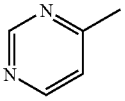 | 104-106° C. |
| 9.3. | 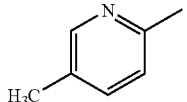 | 234-236° C. as dihydrochloride |
| 9.4. | 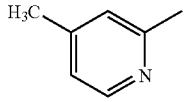 | 2.12(s, 3H), 6.72(d, 1H), 7.33(dd, 1H), 7.92(d, 1H) |
| 9.5. | 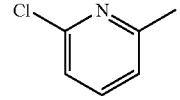 | 2.26(s, 3H), 6.47(m, 2H), 8.03(d, 1H) |
| 9.6. | 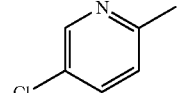 | 238-240° C. as dihydrochloride |
| 9.7. | 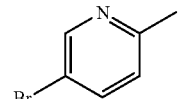 | 6.84(d, 1H), 7.52(dd, 1H), 8.05(d, 1H) |
| 9.8. | 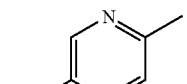 | 6.75(d, 1H), 7.60(d, 1H), 8.12(s, 1H) |
| 9.9. | 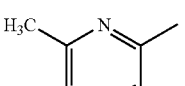 | 86-89° C. |
| 9.10. | 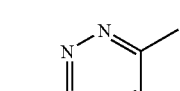 | 2.37(s, 3H), 6.72(d, 1H), 7.87(d, 1H) |
| 9.11. |  | 117-119° C. |

TABLE 9-continued (II)

R¹—N⟨piperidine⟩NH₂

| Example | R¹ | Characterisation (M.p., LC/MS or aromatic protons by ¹H-NMR [DMSO-d₆]) |
|---|---|---|
| 9.12. | 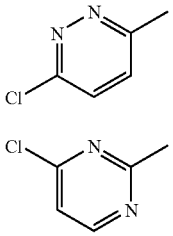 3-chloro-6-methylpyridazine | 135-139° C. |
| 9.13. | 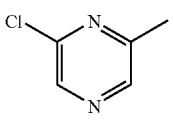 4-chloro-2-methylpyrimidine | 6.65(d, 1H), 8.27(d, 1H) |
| 9.14. | 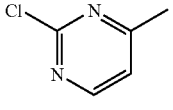 2-chloro-6-methylpyrazine | 7.78(s, 1H), 8.26(s, 1H) |
| 9.15. | 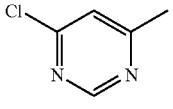 2-chloro-4-methylpyrimidine | 6.80(d, 1H), 8.00(d, 1H) |
| 9.16. | 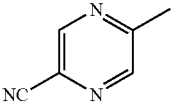 4-chloro-6-methylpyrimidine | 296-303° C. as dihydrochloride |
| 9.17. | 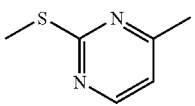 5-methyl-2-cyanopyrazine | [MH]⁺ = 204 |
| 9.18. | 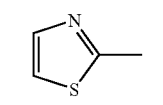 2-methylthio-4-methylpyrimidine | 2.33(s, 3H), 6.51(d, 1H), 7.96(d, 1H) |
| 9.19. | 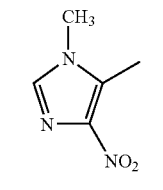 2-methylthiazole | 112-114° C. |
| 9.20. | 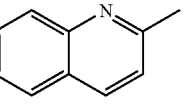 1-methyl-5-methyl-4-nitroimidazole | 167-170° C. |
| 9.21. | 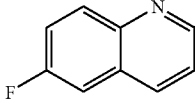 2-methylquinoline | 67-68° C. |
| 9.22. | 6-fluoro-2-methylquinoline | 7.60(m, 2H), 7.72(d, 1H), 8.15(m, 1H), 8.32(1H, d), |

TABLE 9-continued (II)

R¹—N⟨piperidine⟩NH₂

| Example | R¹ | Characterisation (M.p., LC/MS or aromatic protons by ¹H-NMR [DMSO-d₆]) |
|---|---|---|
| 9.23. | 2-methyl-4-quinolinyl (with CH₃ at 4-position) | 260-262° C. as dihydrochloride |
| 9.24. | 1-isoquinolinyl | 253-256° C. as dihydrochloride |
| 9.25. | 2-quinoxalinyl | 7.34(m, 1H), 7.58(m, 2H), 7.79(dd, 1H), 8.81(s, 1H) |
| 9.26. | 2-benzothiazolyl | 7.03(t, 1H), 7.26(t, 1H), 7.42(d, 1H), 7.74(d, 1H) |
| 9.27. | 2-benzoxazolyl | 274-275° C. as dihydrochloride |
| 9.28. | 6-phenyl-3-pyridazinyl | 113-115° C. |
| 9.29. | 1-phenyl-1H-tetrazol-5-yl | 216-223° C. as dihydrochloride |
| 9.30. | 4,6-dimethoxy-1,3,5-triazin-2-yl | 3.70(s, 6H) |

We claim:

1. A compound having the formula:

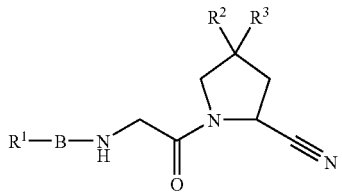

(I)

wherein

R¹ represents a nitrogen-containing aromatic moiety consisting of one or two aromatic rings; which is optionally mono- or disubstituted by a substituent independently selected from the group consisting of C1-4 alkyl, C1-4 alkoxy, halogen, trihalogenomethyl, methylthio, nitro, cyano, amino, and phenyl group;

B represents a group having the formula

 or (1)

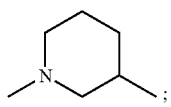 ;

(2)

R² represents a hydrogen atom or a fluorine atom;
R³ represents a fluorine atom;
or a salt, isomer, tautomer, solvate, or hydrate thereof with the proviso that R1 cannot be benzoxazolyl.

2. A compound according to claim 1 wherein said nitrogen-containing aromatic moiety consisting of one or two aromatic rings is selected from the group consisting of a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl or benzisoxazolyl, tetrazolyl, and a triazinyl ring.

3. A compound according to claim 1 wherein R¹ represents a nitrogen-containing aromatic moiety consisting of one or two aromatic rings; which is optionally mono- or disubstituted by a substituent independently selected from the group consisting of C1-4 alkyl, C1-4 alkoxy, halogen, trihalogenomethyl, methylthio, nitro, and cyano.

4. A compound according to claim 3 wherein B represents a group having the formula

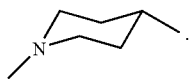

(1)

5. A compound according to claim 3 wherein B represents a group having the formula

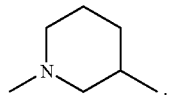

(2)

6. A compound according to claim 3 wherein said nitrogen-containing aromatic moiety consisting of one or two aromatic rings is selected from a pyridyl, pyridazinyl, pyrimidinyl, pyrazinyl, imidazolyl, pirazolyl, thiazolyl, isothiazolyl, oxazolyl, isoxazolyl, oxadiazolyl, quinolinyl, isoquinolinyl, cinnolinyl, phthalazinyl, quinazolinyl, quinoxalinyl, benzimidazolyl, indazolyl, benzothiazolyl, benzisothiazolyl or benzisoxazolyl ring.

7. A compound according to claim 6 wherein B represents a group having the formula

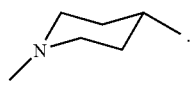

(1)

8. A compound according to claim 6 wherein B represents a group having the formula

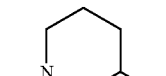

(2)

9. A compound according to claim 4 wherein R¹ represents 2-pyrimidinyl, 2-pyrazinyl, chloro- and cyano-substituted pyridazinyl, or cyano-substituted 2-pyridinyl; and R² represents a fluorine atom.

10. A compound according to claim 5 wherein R¹ represents 2-pyrimidinyl, 2-pyrazinyl, chloro- and cyano-substituted pyridazinyl, or cyano-substituted 2-pyridinyl; and R² represents a fluorine atom.

11. A compound according to claim 1 selected from the group consisting of
(2S)-4,4-Difluoro-1-(2-{[1-(2-pyrazinyl)piperidin-4-yl]amino}acetyl)-2-pyrrolidine carbonitrile,
(2S)-4,4-Difluoro-1-(2-{[1-(5-cyanopyridin-2-yl)piperidin-4-yl]amino}acetyl)-2-pyrrolidine carbonitrile,
(2S)-4,4-Difluoro-1-(2-{[1-(6-chloropyridazin-3-yl)piperidin-4-yl]amino}acetyl)-2-pyrrolidine carbonitrile, and
(2S)-4,4-Difluoro-1-(2-{[1-(6-cyanopyridazin-3-yl)piperidin-4-yl]amino}acetyl)-2-pyrrolidine carbonitrile.

12. A pharmaceutical formulation comprising a compound according to claim 1 and a pharmaceutically acceptable excipient.

13. A pharmaceutical formulation comprising a compound according to claim 3 and a pharmaceutically acceptable excipient.-

14. A pharmaceutical formulation comprising a compound according to claim 6 and a pharmaceutically acceptable excipient.

15. A pharmaceutical formulation comprising a compound according to claim 7 and a pharmaceutically acceptable excipient.

16. A pharmaceutical formulation comprising a compound according to claim 8 and a pharmaceutically acceptable excipient.

17. A pharmaceutical formulation according to claim 12 wherein the compound is selected from the group consisting of (2S)-4,4-difluoro-1-(2-{[1-(2-pyrazinyl)piperidin-4-yl]amino}acetyl)-2-pyrrolidine carbonitrile;

(2S)-4,4-difluoro-1-(2-{[1-(5-cyanopyridin-2-yl)piperidin-4-yl]amino}acetyl)-2-pyrrolidine carbonitrile;

(2S)-4,4-difluoro-1-(2-{[1-(6-chloropyridazin-3-yl)piperidin-4-yl]amino}acetyl)-2-pyrrolidine carbonitrile; and (2S)-4,4-difluoro-1-(2-{[1-(6-cyanopyridazin-3-yl)piperidin-4-yl]amino}acetyl)-2-pyrrolidine carbonitrile.

18. A process for the preparation of a compound according to claim 1, wherein a compound having the formula (II):

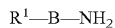   (II)

is reacted with a compound of the formula (III):

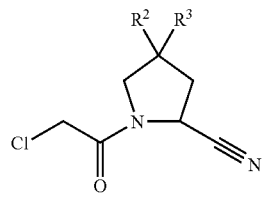   (III)

wherein $R^1$, B, $R^2$ and $R^3$ are as defined in claim 1.

19. A method for the treatment of type II diabetes comprising administering to a patient in need of such treatment an effective amount of a compound according to claim 1.

20. A method for the treatment of type II diabetes comprising administering to a patient in need of such treatment an effective amount of a compound according to claim 3.

21. A method for the treatment of type II diabetes comprising administering to a patient in need of such treatment an effective amount of a compound according to claim 6.

22. A method according to claim 19, wherein the compound is selected from the group consisting of:

(2S)-4,4-difluoro-1-(2-{[1-(2-pyrazinyl)piperidin-4-yl]amino}acetyl)-2-pyrrolidine carbonitrile;

(2S)-4,4-difluoro-1-(2-{[1-(5-cyanopyridin-2-yl)piperidin-4-yl]amino}acetyl)-2-pyrrolidine carbonitrile;

(2S)-4,4-difluoro-1-(2-{[1-(6-chloropyridazin-3-yl)piperidin-4-yl]amino}acetyl)-2-pyrrolidine carbonitrile; and (2S)-4,4-difluoro-1-(2-{[1-(6-cyanopyridazin-3-yl)piperidin-4-yl]amino}acetyl)-2-pyrrolidine carbonitrile.

* * * * *